(12) United States Patent
Gaggar et al.

(10) Patent No.: US 11,738,013 B2
(45) Date of Patent: Aug. 29, 2023

(54) METHODS FOR TREATING HEPATITIS B VIRUS INFECTIONS USING NS5A, NS5B OR NS3 INHIBITORS

(71) Applicant: Gilead Sciences, Inc., Foster City, CA (US)

(72) Inventors: Anuj Gaggar, Redwood City, CA (US); G. Mani Subramanian, Menlo Park, CA (US)

(73) Assignee: Gilead Sciences, Inc., Foster City, CA (US)

( * ) Notice: Subject to any disclaimer, the term of this patent is extended or adjusted under 35 U.S.C. 154(b) by 1252 days.

(21) Appl. No.: 16/304,824

(22) PCT Filed: May 11, 2017

(86) PCT No.: PCT/US2017/032282
§ 371 (c)(1),
(2) Date: Nov. 27, 2018

(87) PCT Pub. No.: WO2017/205078
PCT Pub. Date: Nov. 30, 2017

(65) Prior Publication Data
US 2022/0117952 A1 Apr. 21, 2022

Related U.S. Application Data

(60) Provisional application No. 62/342,787, filed on May 27, 2016.

(51) Int. Cl.
*A61K 31/454* (2006.01)
*A61K 31/498* (2006.01)
*A61K 31/661* (2006.01)

(52) U.S. Cl.
CPC .......... *A61K 31/454* (2013.01); *A61K 31/498* (2013.01); *A61K 31/661* (2013.01)

(58) Field of Classification Search
CPC .................................................. A61K 31/454
See application file for complete search history.

(56) References Cited

FOREIGN PATENT DOCUMENTS

| CN | 104546886 | 4/2015 |
| WO | WO-2014120981 | 8/2014 |
| WO | WO-2014137929 | 9/2014 |

OTHER PUBLICATIONS

De Monte et al., "Direct-acting antiviral treatment in adults infected with hepatitis C virus: Reactivation of hepatitis B virus coinfection as a further challenge", Journal of Clinical Virology, vol. 78, Feb. 28, 2016 (Year: 2016).*
Kumar, "Hepatitis C, Chronic-MSD Manual Professional Edition", MSD Manuals, Aug. 21, 2015 (Year: 2015).*
"Harvoni", FDA, Reference ID: 3642283, Oct. 2014 (Year: 2014).*
Highleyman, "Tenofovir alafenamide works well against Hepatitis B with less effect on bones and kidneys", Aidsmap, Apr. 18, 2016 (Year: 2016).*
"Vemlidy (tenofovir AF)", Medscape, Apr. 1, 2015 (Year: 2015).*
Charlton et al., Ledispavir and Sofosbuvir Plus Ribavirin for Treatment of HCV Infection in Patients with Advanced Liver Disease, 2015, Gastroenterology, vol. 149, pp. 649-659.
Collins et al., "Hepatitis B Virus Reactivation During Successful Treatment of Hepatitis C Virus with Sofosbuvir and Simeprevir: Figure 1", Clinical Infectious Diseases, vol. 61, No. 8, Oct. 15, 2015, pp. 1304-1306.
De Monte et al., "Direct-acting Antiviral Treatment in Adults Infected with Hepatitis C Virus: Reactivation of Hepatitis B Virus Coinfection as a Further Challenge", Journal of Clinical Virology, vol. 78, May 1, 2016, pp. 27-30.
Examination Report for AU Appl. No. 2017271990 dated Apr. 9, 2019, 6 pages.
Fabbri et al., "Reactivation of Occult HBV Infection in an HIV/HCV Co-infected Patient Successfully Treated with Sofosbuvir/Ledipasvir: A Case Report and Review of the Literature", BMC Infectious Diseases, Mar. 1, 2017, vol. 17, No. 1, pp. 1-5.
Gane et al., "International Medical Press—Browse Articles", Jul. 1, 2016, Retrieved from the Internet: URL:https://www/intmedpress.com/journals/avt/abstract.cfm?id=3066&pid=88, retrieved on Jul. 26, 2017.
Guo et al., "Regulation of Hepatitis B Virus Replication by the Phosphatidylinositol 3-Kinase-Akt Signal Transduction Pathway", Journal of Virology, vol. 81, No. 18, Sep. 15, 2007, pp. 10072-10080.
International Search Report and Written Opinion for PCT/US2017/032282 dated Aug. 10, 2017, 15 pages.
Ozaras et al., "Treating Hepatitis B Virus/Hepatitis C Virus Coinfected Patients with Direct-Acting Hepatitis C Virus Antivirals Only is not Safe", Hepatology, vol. 64, No. 5, May 24, 2016, pp. 1825-1827.
Pan et al., "NS5A Protein of HCV Enhances HBV Replication and Resistance to Interferon Response", Biochemical and Biophysical Research Communications, vol. 359, No. 1, Jun. 2, 2007, pp. 70-75.
Perni et al., "Preclinical Profile of VX-950, a Potent, Selective, and Orally Bioavailable Inhibitor of Hepatitis C Virus NS3-4A Serine Protease", 2006, Antimicrobial Agents and Chemotherapy, vol. 50, No. 3, pp. 899-909.
Petersen et al., "Optimal Therapy for Chronic Hepatitis B: Hepatitis B Virus Combination Therapy?", Liver International, vol. 35, Jan. 22, 2015, pp. 114-120.
Pollicino et al., "395 Wild Type HCV-NS5A Protein and its Naturally Occurring Mutants Modulate HBV Replication and Gene Expression ED—Zoulim Fabien", Journal of Hepatology, vol. 42, Apr. 1, 2005, p. 145.

(Continued)

*Primary Examiner* — Andrew D Kosar
*Assistant Examiner* — Gillian A Hutter
(74) *Attorney, Agent, or Firm* — Sheppard Mullin Richter & Hampton LLP

(57) ABSTRACT

Provided are methods for treating hepatitis B virus infections by administering a NS5A inhibitor, NS5B inhibitor, a NS3 inhibitor, or combinations thereof.

21 Claims, 4 Drawing Sheets

(56) References Cited

OTHER PUBLICATIONS

Wyles et al., "International Medical Press—Advanced Publication", Jan. 1, 2017, Retrieved from the Internet: URL:https://www.intmedpress,com/journals/avt/abstract.cfm?id=3181&pid=48, retrieved on Jul. 26, 2017.
Examination Report for Canada Patent Application No. 3,025,633 dated Dec. 17, 2019. 5 pages.
Examination Report for European Patent Application No. 17725086.7 dated Oct. 2, 2020. 10 pages.
Notice of Preliminary Rejection for Korean Patent Application No. 10-2018-7037210 dated Jul. 6, 2020. 8 pages.
Office Action for Chinese Patent Application No. 201780039972.3 dated Jul. 7, 2020. 23 pages.
Official Action for Japanese Patent Application No. 2018-561567 dated Nov. 21, 2019. 14 pages.
Official Action for Japanese Patent Application No. 2020-159362 dated Sep. 29, 2021. 3 pages.
Rejection Decision for Chinese Patent Application No. 201780039972.3 dated Nov. 3, 2021. 11 pages.
Second Office Action for Chinese Patent Application No. 201780039972.3 dated Jan. 11, 2021. 13 pages.
Suzuki, Interferon-free treatment for patients with chronic hepatitis C. Nippon Rinsho, 2015, vol. 73, No. 2, pp. 285-291.
Third Office Action for Chinese Patent Application No. 201780039972.3 dated Jul. 9, 2021. 9 pages.

* cited by examiner

Mean HBsAg Change From Baseline

Mean HBV DNA Change From Baseline

[ (1) ]

METHODS FOR TREATING HEPATITIS B VIRUS INFECTIONS USING NS5A, NS5B OR NS3 INHIBITORS

This application claims the benefit under 35 U.S.C. § 119(e) of the U.S. Provisional Application Ser. No. 62/342,787 filed May 27, 2016, the content of which is hereby incorporated by reference in its entirety.

FIELD

The disclosure relates generally to methods, compounds and compositions for treating hepatitis B virus infections.

BACKGROUND

Worldwide, approximately 400 million people are living with chronic hepatitis B infection (HBV). HBV is an enveloped, partially double-stranded DNA virus. HBV is an infectious disease that affects the liver. Initial symptoms of infection may include vomiting, jaundice, lethargy, dark urine, and abdominal pain. Chronic HBV infection can result in cirrhosis and liver cancer. Currently available therapies can inhibit replication of the virus and minimize liver damage; however, there are no currently available therapies that can clear an HBV infection.

HBV surface antigen (HBsAg) is a protein located in the HBV envelope. It allows HBV virion entry into host cells by binding to the hepatocyte sodium-taurocholate cotransporting polypeptide (NTCP) receptor. HBsAg may also function as a tolerogen, suppressing immune elimination of infected cells. Total HBsAg loss and seroconversion are rarely achieved in chronically infected patients. Inhibiting HBsAg secretion and/or production is thus believed to be a strategy for the treatment of HBV infection, including chronic HBV infection. (Wieland, S. F. & F. V. Chisari, *J. Virol.* (2005), 79, 9369-80; Woltman et al. *PLoS One* (2011), 6, e15324; Op den Brouw et al. *Immunology* (2009b), 126, 280-89).

There remains a need to develop effective treatments for hepatitis B infection.

SUMMARY

It has now been discovered that when a patient is administered inhibitors of certain HCV nonstructural proteins, such as a NS5A inhibitor, a NS5B inhibitor, a NS3 inhibitor, or combinations thereof, the HBV surface antigen (HBsAg) is decreased, thereby treating the patient's HBV infection. Therefore, in one embodiment, is provided a method of treating HBV infection in a human in need thereof, comprising administering to the patient an effective amount of a NS5A inhibitor. In one embodiment, is provided a method of treating HBV infection in a human in need thereof, comprising administering to the patient an effective amount of a NS5B inhibitor. In one embodiment, is provided a method of treating HBV infection in a human in need thereof, comprising administering to the patient an effective amount of a NS3 inhibitor. In yet another embodiment, the patient is administered both an effective amount of a NS5A inhibitor and a NS5B inhibitor and optionally a NS3 inhibitor. In one embodiment, the patient is further administered another anti-HBV agent, such as reverse transcriptase inhibitors. In one embodiment, the patient is co-infected with human immunodeficiency virus (HIV). In one embodiment, the patient is not co-infected with hepatitis C virus (HCV). In one embodiment, the NS5A inhibitor is ledipasvir or velpatasvir. In one embodiment, the NS5B inhibitor is sofosbuvir or mericitabine. In one embodiment, the NS5A inhibitor is ledipasvir and the NS5B inhibitor is sofosbuvir. In one embodiment, the NS3 inhibitor is voxilaprevir. In one embodiment, the anti-HBV agent is tenofovir.

In one embodiment, the patient is administered a combination of either ledipasvir or velpatasvir, together with sofosbuvir and voxilaprevir. In one embodiment, the patient is administered a combination of either ledipasvir or velpatasvir, together with sofosbuvir and tenofovir.

DETAILED DESCRIPTION

Figure 1:
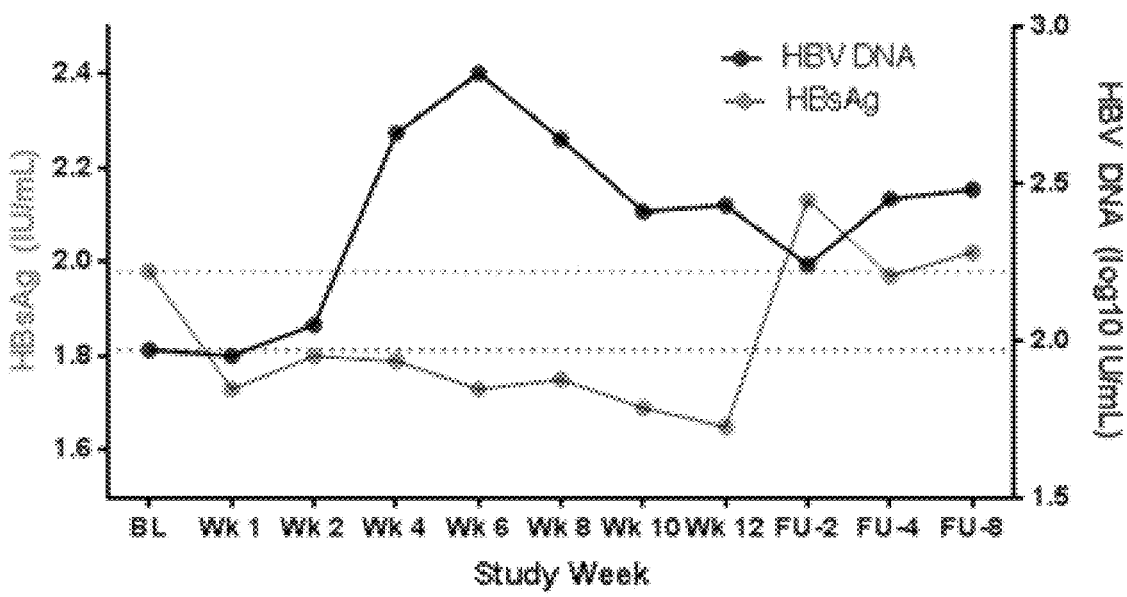
FIG. 1 shows the reduction of HBsAg in a study where 8 pateints were administered a fixed dose combination of ledipasvir and sofosbuvir.

Reference will now be made in detail to certain embodiments of the disclosure, examples of which are illustrated in the accompanying description, structures and formulas. While the disclosure will be described in conjunction with the enumerated embodiments, it will be understood that they are not intended to limit the disclosure to those embodiments. On the contrary, the disclosure is intended to cover all alternatives, modifications, and equivalents, which may be included within the scope of the present disclosure.

I. METHODS

As stated above, it is discovered that administration of inhibitors of certain nonstructural proteins in the hepatitis C virus are useful in reducing HBV surface antigens, thereby treating HBV infected patients.

It is to be understood that the term "treatment" or "treating" means any administration of a compound(s) of the disclosure to a mammal (e.g. a human) having HBV for the purpose of: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

Therefore, in one embodiment, is provided a method of treating HBV infection in a human in need thereof, comprising administering to the patient an effective amount of a NS5A inhibitor. In one embodiment, is provided a method of treating HBV infection in a human in need thereof, comprising administering to the patient an effective amount of a NS5B inhibitor. In one embodiment, is provided a method of treating HBV infection in a human in need thereof, comprising administering to the patient an effective amount of a NS3 inhibitor. In one embodiment is provided a method for treating a hepatitis B virus infection in a human in need thereof comprising administering an effective amount of a NS5A inhibitor and an effective amount of a NS5B inhibitor and optionally a NS3 inhibitor. In one embodiment, the NS5A inhibitor is ledipasvir or velpatasvir. In one embodiment, the NS5A inhibitor is ledipasvir. In one embodiment, the NS5B inhibitor is sofosbuvir or mericitabine. In one embodiment, the NS5A inhibitor is ledipasvir and the NS5B inhibitor is sofosbuvir. In this embodiment, the patient is administered about 90 milligrams of ledipasvir and about 400 milligrams of sofosbuvir. In certain embodiments, the inhibitors are administered together. In other embodiments, the inhibitors are administered separately.

In one embodiment, the NS3 inhibitor is voxilaprevir.

In one embodiment, the patient is administered a combination of either ledipasvir or velpatasvir, together with sofosbuvir and voxilaprevir.

In one embodiment, the patient is further administered another anti-HBV agent. In one embodiment, the patient is administered a NS5A inhibitor and an anti-HBV agent. In one embodiment, the patient is administered a NS5B inhibitor and an anti-HBV agent. In one embodiment, the patient is administered a NS3 inhibitor and an anti-HBV agent. In one embodiment, the patient is adminstered a NS5A inhibitor, a NS5B inhibitor, an anti-HBV agent and optionally a NS3 inhibitor. In one embodiment, the NS5A inhibitor is ledipasvir or velpatasvir. In one embodiment, the NS5A inhibitor is ledipasvir. In one embodiment, the NS5B inhibitor is sofosbuvir or mericitabine. In one embodiment, the NS5A inhibitor is ledipasvir and the NS5B inhibitor is sofosbuvir. In one embodiment, the anti-HBV agent is tenofovir alafenamide. In one embodiment, the NS3 inhibitor is voxilaprevir. In one embodiment, the patient is administered a combination of either ledipasvir or velpatasvir, with sofosbuvir, voxilaprevir and tenofovir alafenamide. In one embodiment, the patient is administered about 90 milligrams of ledipasvir, about 400 milligrams of sofosbuvir and about 25 mg of tenofovir alafenamide. In certain embodiments, the inhibitors are administered together. In other embodiments, the inhibitors are administered separately.

In one embodiment, the patient is co-infected with human immunodeficiency virus (HIV). In one embodiment, the patient is not co-infected with hepatitis C virus (HCV).

In one embodiment, the inhibitor(s) inhibit HBsAG production or secretion. In one embodiment, the inhibitor(s) inhibit HBV gene expression. In one embodiment, the inhibitor(s) are useful for the treatment or prophylaxis of HBV infection. In one embodiment, the inhibitor(s) inhibit HBV DNA production. In one embodiments, the inhibitor(s) inhibit HBV DNA replication.

In one embodiment is a pharmaceutical composition comprising a NS5A inhibitor for use in treating a hepatitis B virus infection in a human. In one embodiment is a composition comprising a NS5A inhibitor for use in the preparation of a medicament useful in treating a hepatitis B virus infection in a human. In one embodiment, the composition further comprises another anti-HBV agent.

In one embodiment is a pharmaceutical composition comprising a NS5B inhibitor for use in treating a hepatitis B virus infection in a human. In one embodiment is a composition comprising a NS5B inhibitor for use in the preparation of a medicament useful in treating a hepatitis B virus infection in a human. In one embodiment, the composition further comprises another anti-HBV agent.

In one embodiment is a pharmaceutical composition comprising a NS3 inhibitor for use in treating a hepatitis B virus infection in a human. In one embodiment is a composition comprising a NS3 inhibitor for use in the preparation of a medicament useful in treating a hepatitis B virus infection in a human. In one embodiment, the composition further comprises another anti-HBV agent.

In one embodiment is a pharmaceutical composition comprising a NS5A inhibitor and a NS5B inhibitor and optionally a NS3 inhibitor for use in treating a hepatitis B virus infection in a human. In one embodiment, is a composition comprising a NS5A inhibitor and a NS5B inhibitor and optionally a NS3 inhibitor for use in the preparation of a medicament useful in treating a hepatitis B virus infection in a human. In one embodiment, the composition further comprises another anti-HBV agent.

II. COMPOUNDS

The protein products of the HCV gene include the nonstructural proteins NS2, NS3, NS4A and NS4B, and NS5A and NS5B. In HCV infected cells, NS5A is produced as part of the viral polyprotein. Once cleaved from the polyprotein, NS5A localizes to membranes where it binds to the newly synthesized viral RNA and participates in genome replication, in part through interactions with the viral RNA-dependent RNA polymerase NS5B. NS5A inhibitors are compounds that target the HCV-encoded NS5A gene product. NS3 is a viral nonstructural protein that is 70 kDa cleavage product of the hepatitis C virus polyprotein. It acts as a serine protease.

It should be noted that the term compound or inhibitor is used interchangeably throughout.

HCV NS5B polymerase is required for the synthesis of a double-stranded RNA from a single-stranded viral RNA that serves as a template in the replication cycle of HCV. Inhibition of HCV NS5B polymerase prevents formation of the double-stranded HCV RNA. Examples of both NS5A, NS5B, and NS3 compounds are described below.

A. NS5A Inhibitors

In one embodiment, the NS5A inhibitor is a compound described in PCT Publication No. WO2010/132601, which is hereby incorporated by reference in its entirety. It is contemplated that the NS5A inhibitor may also be selected from compounds disclosed in U.S. Pat. No. 9,156,823; US 2013/0309196 (WO 2013/173488); or US 2014/0178336 (or WO 2014/100500), all of which are incorporated by reference in their entirety.

In one embodiment, the NS5A inhibitor is a compound of Formula I (described in WO2010/132601):

$$J-Y-J \qquad \text{Formula I}$$

wherein:
    Y is -L-L-, -M-W-M- or $Y^1$;
    J is T-P—, —P-T or $-J^m$;
    W is a bond or $—W^r—$;
    L is -M-A-, -A-M-, or $-L^n$;
    T is R9-Z—, —Z—$R^9$, or $-T^p$;
    $R^9$ is E-V-, or —V-E, or —$R^{9q}$;
    each A is selected from $-A^s$;
    each M is selected from $-M^r$;
    each P is selected from —$P^u$;
    each Z is selected from —$Z^v$;
    each V is selected from —$V^w$;
    each E is selected from $-E^x$;
    each m is 1
    each n is 0, 1, 2, 3, 4, 5, 6, 7, 9, or 10;
    each p is 1, 2, 3, 4, 5, 6, 7, or 8;
    each q is 0, 1, 2, or 3;
    each r is 1, 2, 3, 4, 5, 6, 7, 8, 9, 10, 11, 12, 13, 14, 15, 16, 17, 18, 19, or 20;
    each s is 0, 1, 2, 3, 4, 5, 6, 7, 8, 9, 10, 11, 12, 13, 14, 15, 16, 17, 18, or 21;
    each t is 0, 1, 2, 3, 4, 5, 6, 7, 8, 9, 10, or 11;
    each u is 0, 1, 2, 3, 4, 5, 6, 7, 8, 10, 11, 12, 13, 14, 15, 16, 17, 18, or 19;

each v is 0, 1, 2, 3, 4, 5, or 6;
each w is 0, 1, 2, 3, 4, 5, 6, 7, 8, 9, 10, 11, 12, 13, 14, 15, 16, 17, 18, 19, 20, 21, 22, 23, or 24;
each x is 0, 1, 2, 3, 4, 5, 6, or 7;
each y is 0, 1, or 2;
wherein P is connected to M, L, or $Y^y$; A is connected to A or L; M is connected to P or J; Z is connected to P; V is connected to Z; and when W is a bond M is connected to M;
each $J^1$ is independently a fused bicyclic saturated, partially unsaturated, or aromatic heterocyclic ring system that is substituted with one or more —N($R^{L7}$)C(=O)O$R^{L7}$, and that is optionally substituted with one or more groups independently selected from oxo, halo, —$R^{L7}$, —O$R^{L7}$, —S$R^{L7}$, —CF$_3$, —CCl$_3$, —OCF$_3$, —CN, —NO$_2$, —N($R^{L7}$)C(=O)$R^{L7}$, —C(=O)$R^{L7}$, —OC(=O)$R^{L7}$, —C(O)O$R^{L7}$, —C(=O)NR$^{L7}$, —S(=O)$R^{L7}$, —S(=O)$_2$O$R^{L7}$, —S(=O)$_2$$R^{L7}$, —OS(=O)$_2$O$R^{L7}$, —S(=O)$_2$N$R^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;
each $R^{L7}$ is independently —H, alkyl, aryl, arylalkyl, or heterocycle;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $L^0$ is independently:

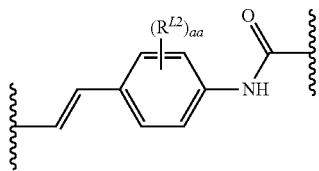

wherein:
each $R^{L2}$ is independently selected from hydrogen, alkenyl, alkoxy, alkyl, halo, and haloalkyl; and
each aa is independently 1, 2, 3, or 4;
each $L^1$ is independently:

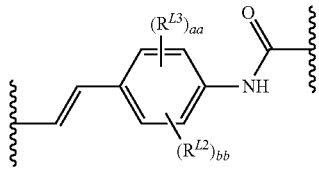

wherein:
each $R^{L2}$ is independently selected from hydrogen, alkenyl, alkoxy, alkyl, halo, and haloalkyl;
each $R^{L3}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each R$^4$ is independently selected from H, alkyl, haloalkyl, aryl, and arylalkyl;
each bb is 0, 1, 2, 3, or 4; each aa is 1, 2, 3, or 4; and the sum of bb and aa is 1, 2, 3, or 4;

each $L^2$ is independently:
wherein:

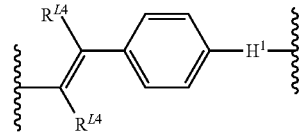

the phenyl ring shown in $L^2$ is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{L4}$ is independently —H, alkyl, aryl, arylalkyl, or heterocycle;
each R$^4$ is independently selected from H, alkyl, haloalkyl, aryl, and arylalkyl;
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and
each H1 is a 5 membered saturated, partially unsaturated, or aromatic ring comprising one or more heteroatoms.
each $L^3$ is independently a fused-bicyclic saturated, partially unsaturated, or aromatic heterocyclic ring system that is optionally substituted with one or more groups independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R$^4$ is independently selected from H, alkyl, haloalkyl, aryl, and arylalkyl; and
$R^a$ and $R^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $L^4$ is independently a fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R, (NR$^a$R$^b$)alkyl, (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each R$^4$ is independently selected from H, alkyl, haloalkyl, aryl, and arylalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L$^5$ is independently a —CR=CR-fused bicyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each R is independently selected from H or alkyl;

each R$^4$ is independently selected from H, alkyl, haloalkyl, aryl, and arylalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L$^6$ is independently a —CR=CR-fused-tricyclic saturated, partially unsaturated, or aromatic heterocyclic ring system that is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, (NR$^a$R$^b$)carbonyl, cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;

each R is independently selected from H or alkyl;

each R$^4$ is independently selected from H, alkyl, haloalkyl, aryl, and arylalkyl; and R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L$^7$ is independently:

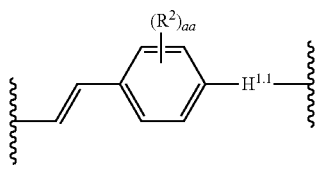

wherein:
each H$^{1.1}$ is independently a fused-bicyclic saturated, partially unsaturated, or aromatic heterocyclic ring system that is optionally substituted with one or more R$^2$ each R$^2$ is independently selected from halo, —R$^{L7}$, —OR$^{L7}$, —SR$^{L7}$, —N(R$^{L7}$)$_2$, —CF$_3$, —CCl$_3$, —OCF$_3$, —CN, —NO$_2$, —N(R$^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)$_2$OR$^{L7}$, —OS(=O)$_2$OR$^{L7}$, and —S(=O)$_2$NR$^{L7}$;

each R$^L$ is independently —H, alkyl, aryl, arylalkyl, or heterocycle; and each aa is independently 1, 2, 3, or 4;

each L$^9$ is independently a fused-tetracyclic saturated, partially unsaturated, or aromatic heterocyclic ring system that is optionally substituted with one or more groups independently selected from oxo, halo, —R$^{L7}$, —OR$^{L7}$, —SR$^{L7}$, —CF$_3$, —CCl$_3$, —OCF$_3$, —CN, —NO$_2$, —N(R$^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)$_2$OR$^{L7}$, —S(=O)$_2$R$^{L7}$, —OS(=O)$_2$OR$^{L7}$, —S(=O)$_2$NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L$^{10}$ is independently a fused-pentacyclic saturated, partially unsaturated, or aromatic heterocyclic ring system that is optionally substituted with one or more groups independently selected from oxo, halo, —R$^{L7}$, —OR$^{L7}$, —SR$^{L7}$, —CF$_3$, —CCl$_3$, —OCF$_3$, —CN, —NO$_2$, —N(R$^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)$_2$OR$^{L7}$, —S(=O)$_2$R$^{L7}$, —OS(=O)$_2$OR$^{L7}$, —S(=O)$_2$NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^L$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each L$^{11}$ is independently a six-ring fused saturated, partially unsaturated, or aromatic heterocyclic ring system that is optionally substituted with one or more groups independently selected from oxo, halo, —R$^{L7}$, —OR$^{L7}$, —SR$^{L7}$, —CF$_3$, —CCl$_3$, —OCF$_3$, —CN, —NO$_2$, —N(R $^{L7}$)C(=O)R$^{L7}$, —C(=O)R$^{L7}$, —OC(=O)R$^{L7}$, —C(O)OR$^{L7}$, —C(=O)NR$^{L7}$, —S(=O)R$^{L7}$, —S(=O)$_2$OR$^{L7}$, —S(=O)$_2$R$^{L7}$, —OS(=O)$_2$OR$^{L7}$, —S(=O)$_2$NR$^{L7}$, alkoxyalkyl, arylalkoxycarbonyl, halo, haloalkyl, hydroxyalkyl, —NR$^a$R$^b$, (NR$^a$R$^b$)alkyl, and (NR$^a$R$^b$)carbonyl;

each R$^{L7}$ is independently —H, alkyl, aryl, arylalkyl, or heterocycle;

R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;

each R9$^0$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl;

$R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, $(NR^eR^f)$alkyl, $(NR^eR^f)$alkylcarbonyl, $(NR^eR^f)$carbonyl, $(NR^eR^f)$sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

$R^X$ and $R^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and $(NR^XR^Y)$carbonyl, wherein Rx and $R^Y$ are independently selected from hydrogen and alkyl;

each $R9^1$ is independently —N($R^{9a}$)—NHC(=O)O—$R^{9b}$, wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO$_2$alkyl, cycloalkylalkylSO$_2$alkyl, cyanoalkyl, haloalkyl, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclyl, heterocyclylcarbonylalkyl, hydroxyalkyl, NRRCOalkyl, wherein each R is independently selected from hydrogen and alkyl;

and wherein arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; $R^{9b}$ is independently H, alkyl, aryl, haloalkyl, or arylalkyl;

each $R9^2$ is independently —N($R^{9a}$)—NHC(=O)$NR^{9b}{}_2$; wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO$_2$alkyl, cycloalkylalkylSO$_2$alkyl, cyanoalkyl, haloalkyl cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —$(NR^XR^Y)$alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, $(NR^XR^Y)$alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; $R^{9b}$ is independently H, alkyl, aryl, haloalkyl, or arylalkyl;

each $R9^3$ is independently —N($R^{9a}$)—NHC(=O)$R^{9b}$, wherein each $R^{9a}$ is independently arylalkyl, alkyl, alkenyl, alkynyl, aryl, arylalkyl, arylalkenyl, arylalkoxy, halocycloalkyl, (cycloalkyl)alkenyl, (cycloalkyl)alkoxy, alkylSO$_2$alkyl, cycloalkylalkylSO$_2$alkyl, cyanoalkyl, haloalkyl, cycloalkylalkyl, cycloalkyl, alkoxyalkyl, alkoxyalkylcarbonylalkyl, alkoxycarbonylalkyl, alkylsulfanylalkyl, aryalkoxyalkylcarbonylalkyl, carboxyalkyl, heterocyclylalkyl, heterocyclyl, heterocyclylcarbonylalkyl, hydroxyalkyl, NRRCOalkyl, wherein each R is independently selected from hydrogen and alkyl; and where in arylalkyl the alkyl can be substituted with up to three aryl groups, and the alkyl part of the arylalkyl is further optionally substituted with one or two additional groups independently selected from alkoxy, alkylcarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —NR$^X$R$^Y$, —(NR$^X$R$^Y$)alkyl, oxo, and —P(O)OR$_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^X$R$^Y$, —(NR$^X$R$^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro; $R^{9b}$ is independently H, alkyl, aryl, haloalkyl, or arylalkyl;

each $A^0$ is independently:

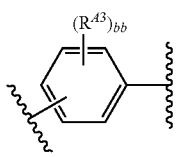

wherein:
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl; and each bb is independently 0, 1, 2, 3, or 4; or each $A^0$ is independently a six-membered heteroaromatic ring containing one, two, or three nitrogen atoms, which ring is optionally substituted with 1, 2, 3, or 4 $R^{43}$ groups;

each $A^1$ is independently:

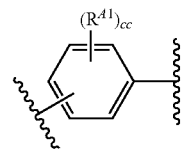

wherein:
each $R^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo; and
each $R^4$ is independently selected from H, alkyl, haloalkyl, aryl, and arylalkyl;
each cc is independently 1, 2, 3, or 4 each $A^2$ is independently:

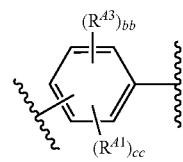

wherein:
each $R^{41}$ is independently selected from cyano, nitro, SOR$^4$, SO$_2$R$^4$, -alkylSO$_2$R$^4$, haloalkoxy, cyanoalkyl, NR$^4$SO$_2$R$^4$, cycloalkyl, (halo)cycloalkyl, heterocycle, (cycloalkyl)alkyl, (heterocycle)alkyl, wherein each alkyl, heterocycle and cycloalkyl is optionally substituted with one or more halo;
each $R^{43}$ is independently selected from alkoxy, alkoxyalkyl, alkoxycarbonyl, alkyl, arylalkoxycarbonyl, carboxy, formyl, halo, haloalkyl, hydroxy, hydroxyalkyl, —NR$^a$R$^b$, (NR$^a$R$^b$)alkyl, and (NR$^a$R$^b$)carbonyl; R$^a$ and R$^b$ are each independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each $R^4$ is independently selected from H, alkyl, haloalkyl, aryl, and arylalkyl;
R$^a$ and R$^b$ are independently selected from the group consisting of hydrogen, alkenyl, alkyl, alkylcarbonyl, aryl, arylalkyl, arylalkylcarbonyl, cycloalkyl, cycloalkylalkyl, heterocyclyl, and heterocyclylalkyl;
each bb is 0, 1, 2, 3, or 4; each cc is 1, 2, 3, or 4; and the sum of bb and cc is 1, 2, 3, or 4;

each $A^3$ is independently a six-membered heteroaromatic ring containing one, two, or three nitrogen atoms, which ring is substituted with one or more R groups, and which ring is optionally substituted with one or more $R^{43}$ groups;

each $A^4$ is independently:

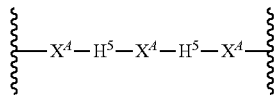

wherein:
each $H^5$ is independently a phenyl ring or a six-membered heteroaromatic ring, which $H^5$ is optionally substituted with one or more groups independently selected from $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^5$ is independently:

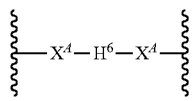

wherein:
each $H^6$ is independently a phenyl ring or a six-membered heteroaromatic ring, which $H^6$ is optionally substituted with one or more groups independently selected from $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent; provided that at least one $X^4$ is present and each R is independently selected from H or alkyl;

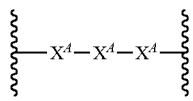

each $A^6$ is independently:
wherein:
each $X^4$ is independently O, NR, SO, $SO_2$, C(=O), NRC(=O), C(=O)NR, CR=CR, allenyl, alkynyl, or absent; provided that at least one $X^4$ is present and each R is independently selected from H or alkyl;

each $A^7$ is independently:

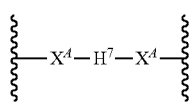

wherein:
each $H^7$ is independently a five-membered heteroaromatic ring, which $H^7$ is
optionally substituted with one or more groups independently selected from $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent; and each R is independently selected from H or alkyl;

each $A^8$ is independently:

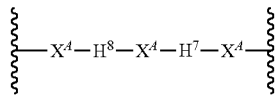

wherein:
each $H^7$ is independently a five-membered heteroaromatic ring, which $H^7$ is optionally substituted with one or more groups independently selected from $R^{41}$ and $R^{43}$;
each $H^8$ is independently a phenyl ring, which is optionally substituted with one or more groups independently selected from $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^9$ is independently:

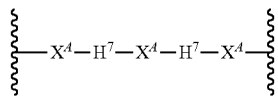

wherein:
each $H^7$ is independently a five-membered heteroaromatic ring, which $H^7$ is optionally substituted with one or more groups independently selected from $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{10}$ is independently:

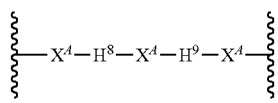

wherein:
each $H^8$ is independently a phenyl ring, which is optionally substituted with one or more groups independently selected from $R^{41}$ and $R^{43}$;
each $H^9$ is independently a six-membered heteroaromatic ring, which is optionally substituted with one or more groups independently selected from $R^{41}$ and $R^{43}$; and
each $X^4$ is independently O, NR, SO, $SO_2$, C(=O), NRC(=O), C(=O)NR, CR=CR, NRC(=O)NR, allenyl, alkynyl, or absent and each R is independently selected from H or alkyl;

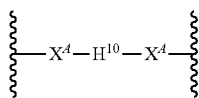

each $A^{11}$ is independently:
  wherein:
    each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
    each $H^{10}$ is independently a 5-15 carbon unsaturated, partially unsaturated or saturated bicyclic ring system that is optionally fused to an aryl, which $H^{10}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, $-NR^aR^b$, $(NR^aR^b)$alkyl, and $(NR^aR^b)$carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
    each $R^4$ is independently selected from H, alkyl, haloalkyl, aryl, and arylalkyl each $A^{12}$ is independently:

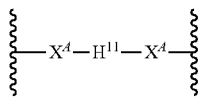

wherein:
    each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;
    each $H^{1.1}$ is independently a 5-15 carbon unsaturated, partially unsaturated or saturated bicyclic ring system that contains one or more heteroatoms that is optionally fused to an aryl, which $H^{1.1}$ is optionally substituted with one or more groups independently selected from oxo, alkoxy, alkoxyalkyl, alkoxycarbonyl, alkyl, arylalkoxycarbonyl, carboxy, formyl, halo, haloalkyl, hydroxy, hydroxyalkyl, $-NR^aR^b$, $(NR^aR^b)$alkyl, and $(NR^aR^b)$carbonyl, cyano, nitro, $SOR^4$, $SO_2R^4$, -alkyl$SO_2R^4$, haloalkoxy, cyanoalkyl, $NR^4SO_2R^4$, cycloalkyl, (halo)cycloalkyl, heterocycle, (cycloalkyl)alkyl, and (heterocycle)alkyl, wherein each alkyl, heterocycle and cycloalkyl is optionally substituted with one or more halo; and
    each $R^4$ is independently selected from H, alkyl, haloalkyl, aryl, and arylalkyl; and

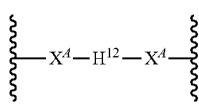

each $A^{13}$ is independently:
  wherein:
    each $H^{12}$ is independently a fused aromatic bicyclic carbocycle, which is optionally substituted with one or more groups independently selected from $R^{41}$ and $R^{43}$; and
    each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

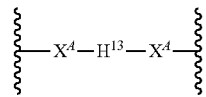

each $A^{14}$ is independently:
  wherein:
    each $H^{13}$ is independently a fused aromatic bicyclic heterocycle that comprises at least one heteroatom in the ring system, which ring system is optionally substituted with one or more groups independently selected from $R^{41}$ and $R^{43}$; and
    each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{15}$ is independently:

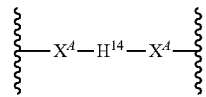

wherein:
    each $H^{14}$ is independently a fused unsaturated, partially unsaturated or saturated tricyclic carbocycle which is optionally substituted with one or more groups independently selected from oxo, $R^{41}$ and $R^{43}$; and
    each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

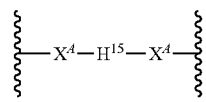

each $A^{16}$ is independently:
  wherein:
    each $H^{15}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and
    each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{17}$ is independently:

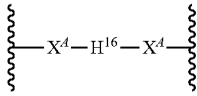

wherein:
- each $H^{16}$ is independently a fused bicyclic carbocyclic ring system wherein one ring is aromatic and another ring is partially or fully saturated, which ring system is optionally substituted with one or more groups independently selected from oxo, $R^{41}$ and $R^{43}$; and
- each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{18}$ is independently:

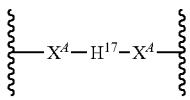

wherein:
- each $H^7$ is independently a fused bicyclic ring system comprising at least one heteroatom, wherein one ring is aromatic and another ring is partially or fully saturated, which ring system is optionally substituted with one or more groups independently selected from oxo, $R^{41}$ and $R^{43}$; and
- each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $A^{21}$ is independently:

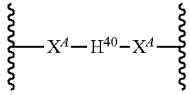

wherein:
- each $H^{40}$ is independently an anti-aromatic monocyclic or fused carbocyclic ring system, which carbocyclic ring system is optionally substituted with one or more groups independently selected from $R^{41}$ and $R^{43}$; and
- each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^1$ is independently —$X^A$—:
wherein:
- each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

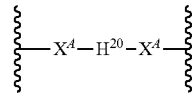

each $W^2$ is independently:
wherein:
- each $H^{20}$ is independently a fused aromatic bicyclic carbocycle, which is optionally substituted with one or more groups independently selected from $R^{41}$ and $R^{43}$; and
- each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^3$ is independently:

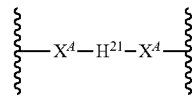

wherein:
- each $H^{21}$ is independently a fused bicyclic carbocyclic ring system wherein one ring is aromatic and another ring is partially or fully saturated, which ring system is optionally substituted with one or more groups independently selected from oxo, $R^{41}$ and $R^{43}$; and
- each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^4$ is independently:

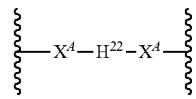

wherein:
- each $H^{22}$ is independently a fused aromatic bicyclic heterocycle that comprises at least one heteroatom in the ring system, which ring system is optionally substituted with one or more groups independently selected from $R^{41}$ and $R^{43}$; and
- each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

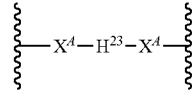

each $W^5$ is independently:
wherein:
- each $H^{23}$ is independently a fused bicyclic ring system comprising at least one heteroatom, wherein one ring is aromatic and another ring is partially or fully saturated, which ring system is optionally substituted with one or more groups independently selected from oxo, $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^6$ is independently:

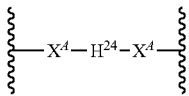

wherein:
each $H^{24}$ is independently a fused unsaturated, partially unsaturated or saturated tricyclic carbocycle, which is optionally substituted with one or more groups independently selected from oxo, $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

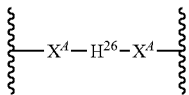

each $W^7$ is independently:

wherein:
each $H^{26}$ is independently a 5-15 carbon unsaturated, partially unsaturated or saturated bicyclic ring system which ring system is optionally substituted with one or more groups independently selected from oxo, $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^8$ is independently:

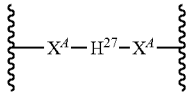

wherein:
each $H^{27}$ is independently a fused unsaturated, partially unsaturated or saturated tricyclic heterocycle that comprises at least one heteroatom in the ring system, which ring system is optionally substituted with one or more groups independently selected from $R^{41}$ and $R^{43}$; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^9$ is independently:

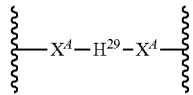

wherein:
each $H^{29}$ is independently a 5-15 carbon unsaturated, partially unsaturated or saturated bicyclic ring system that contains one or more heteroatoms; and each $X^A$ is independently O, NR, SO, $SO_2$, C(=O), NRC(=O), C(=O)NR, CR=CR, NRC(=O)NR, allenyl, alkynyl, or absent and each R is independently selected from H or alkyl;

each $W^{10}$ is independently —$H^{30}$=C=$H^{31}$—
wherein each of —$H^{30}$ and $H^{31}$ is independently a saturated 6-membered heterocyclic ring comprising one or more heteroatoms, which ring is optionally substituted with oxo;

each $W^{11}$ is independently —$H^{32}$=C=$H^{33}$—
wherein each of —$H^{32}$ and $H^{33}$ is independently a saturated 5-membered heterocyclic ring comprising one or more heteroatoms, which ring is optionally substituted with oxo;

each $W^{12}$ is independently an anti-aromatic monocyclic or fused carbocyclic ring system, which carbocyclic ring system is optionally substituted with one or more groups independently selected from $R^{41}$ and $R^{43}$;

each $W^{13}$ is independently a phenyl ring that is optionally substituted with one or more groups independently selected from $R^{41}$ and $R^{43}$;

each $W^{14}$ is independently a 5 or 6 membered heteroaryl ring that is optionally substituted with one or more groups independently selected from $R^{41}$ and $R^{43}$;

each $W^{15}$ is independently a fused unsaturated, partially unsaturated or saturated tetracyclic carbocyclic ring, which ring system is optionally substituted with one or more groups independently selected from oxo, $R^{41}$ and $R^{43}$;

each $W^{16}$ is independently a fused unsaturated, partially unsaturated or saturated tetracyclic heterocycle that comprises at least one heteroatom in the ring system, which ring system is optionally substituted with one or more groups independently selected from oxo, $R^{41}$ and $R^{43}$;

each $W^{17}$ is independently a fused unsaturated, partially unsaturated or saturated pentacyclic carbocyclic ring system, which ring system is optionally substituted with one or more groups independently selected from oxo, $R^{41}$ and $R^{43}$;

each $W^{18}$ is independently a fused unsaturated, partially unsaturated or saturated pentacyclic heterocycle that comprises at least one heteroatom in the ring system, which ring system is optionally substituted with one or more groups independently selected from oxo, $R^{41}$ and $R^{43}$;

each $W^{19}$ is independently a fused unsaturated, partially unsaturated or saturated hexacyclic carbocyclic ring system, which ring system is optionally substituted with one or more groups independently selected from oxo, $R^{41}$ and $R^{43}$;

each $W^{20}$ is independently a fused unsaturated, partially unsaturated or saturated hexacyclic heterocycle that comprises at least one heteroatom in the ring system, which ring system is optionally substituted with one or more groups independently selected from oxo, $R^{41}$ and $R^{43}$;

each M⁰ is independently a five membered heteroaryl group optionally substituted with one or more alkoxycarbonyl, alkyl, arylalkoxycarbonyl, carboxy, haloalkyl, (NR$^a$R$^b$)carbonyl and trialkylsilylalkoxyalkyl;

each M¹ is independently selected from —C(=O)NH—, —C(=O)NH—C(R$^M$)$_2$—, —NHC(=O)—, —C(R$^M$)$_2$NHC(=O)—, —NHC(=O)NR$^M$—, —NHC(=O)O—; wherein each R$^M$ is independently selected from H and alkyl;

each M² is independently a six-membered heteroaromatic ring, which is optionally substituted with one or more groups independently selected from R$^{41}$ and R$^{43}$;

each M³ is independently:

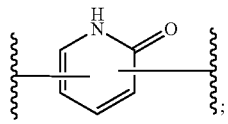

each M⁴ is independently:

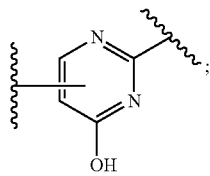

each M⁵ is independently:

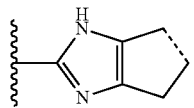

wherein the bond designated with --- is fused to a ring defined for P;

each M⁶ is independently a bicyclic bridged ring system comprising 5-15 atoms wherein at least one of the atoms is a heteroatom;

each M⁷ is independently a pyrid-di-yl;

each M⁸ is independently partially saturated or a saturated five-membered ring that comprises one or more heteroatoms and that is optionally substituted with one or two oxo;

each M⁹ is independently a fused-bicyclic saturated, partially unsaturated, or aromatic heterocyclic ring system that is optionally substituted with one or more R$^{P11}$;

each M¹⁰ is independently a five membered heteroaryl group substituted with at least one alkoxy, cycloalkyl, cyano, alkylsulfonyl, arylsulfonyl, NR$^h$R$^h$, (NR$^h$R$^h$)sulfonyl, heterocyclylsulfonyl, heteroarylsulfonyl, haloalkoxy, alkoxyalkoxy, haloalkoxyalkyloxy, cycloalkoxyalkoxy, aryloxyalkoxy, heteroaryloxyalkoxy, heterocyclyloxyalkyloxy, (NR$^h$R$^h$)alkoxy, cyanoalkoxy, cycloalkoxy, heterocyclyl, alkoxyalkyl, cycloalkoxyalkyl, (NR$^h$R$^h$)alkyl, wherein each R$^h$ is independently —H, alkyl, alkoxyamino, aryl, arylalkyl, heterocycle, heterocyclyloxy, alkenyl, alkenyloxy, alkynyl, alkoxyalkyl, haloalkyl, cyanoalkyl, haloalkoxyalkyl, and sulfonylalkyl; and wherein the five membered ring is also optionally substituted with one or more alkoxycarbonyl, alkyl, arylalkoxycarbonyl, carboxy, haloalkyl, and (NR$^a$R$^b$)carbonyl;

each M¹¹ is independently a fused-tricyclic saturated, partially unsaturated, or aromatic heterocyclic ring system that is optionally substituted with one or more oxo, halo, —R$^{M7}$, —OR$^{M7}$, —SR$^{M7}$, —N(R$^{M7}$)$_2$, —CF$_3$, —CCl$_3$, —OCF$_3$, —CN, —NO$_2$, —N(R$^{M7}$)C(=O)R$^{M7}$, —C(=O)R$^{M7}$, —OC(=O)R$^{M7}$, —C(O)OR$^{M7}$, —C(=O)NR$^{M7}$, —S(=O)R$^{M7}$, —S(=O)$_2$OR$^{M7}$, —S(=O)$_2$R$^{M7}$, —OS(=O)$_2$OR$^{M7}$, or —S(=O)$_2$NR$^{M7}$; each R$^{M7}$ is independently —H, alkyl, aryl, arylalkyl, or heterocycle;

each M¹² is independently a fused-pentacyclic, hexacyclic, or heptacyclic partially unsaturated, or aromatic heterocyclic ring system that is optionally substituted with one or more oxo halo, —R$^{M7}$, —OR$^{M7}$, —SR$^{M7}$, —N(R$^{M7}$)$_2$, —CF$_3$, —CCl$_3$, —OCF$_3$, —CN, —NO$_2$, —N(R$^{M7}$)C(=O)R$^{M7}$, —C(=O)R$^{M7}$, —OC(=O)R$^{M7}$, —C(O)OR$^{M7}$, —C(=O)NR$^{M7}$, —S(=O)R$^{M7}$, —S(=O)$_2$OR$^{M7}$, —S(=O)$_2$R$^{M7}$, —OS(=O)$_2$OR$^{M7}$, or —S(=O)$_2$NR$^{M7}$;

each R$^{M7}$ is independently —H, alkyl, aryl, arylalkyl, or heterocycle;

each P⁰ is independently:

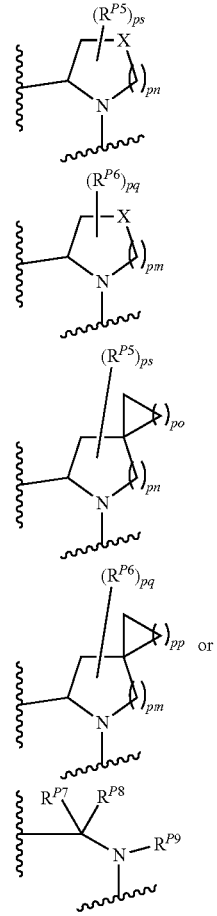

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; $R^{Pa}$ and $R^{Pb}$ are each independently H, alkyl, aryl, or arylalkyl; or $R^{Pa}$ and $R^{Pb}$ taken together with the atom to which they are attached form a heterocycle;

pq and ps are independently 0, 1, 2, 3, or 4;
pm and pn are independently 0, 1, or 2;
po and pp are independently 1, 2, or 3;

$R^{P7}$ and $R^{P8}$ are each independently selected from hydrogen, alkenyl, alkoxyalkyl, alkyl, haloalkyl, and ($NR^{Pa}R^{Pb}$)alkyl; or $R^{P7}$ and $R^{P8}$, together with the carbon atom to which they are attached, form a five or six membered saturated ring optionally containing one or two heteroatoms selected from $NR^{PZ}$, O, and S; wherein $R^{PZ}$ is selected from hydrogen and alkyl;

$R^{P9}$ is selected from hydrogen and alkyl;
each $P^1$ is independently:

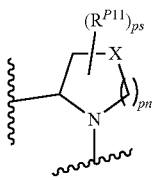

wherein:
X is selected from O, S, S(O), $SO_2$, $CH_2$, $CHR^{P10}$, and $C(R^{P10})_2$; provided that when pn is 0, X is selected from $CH_2$, $CHR^{P10}$, and $C(R^{P10})_2$;

each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

at least one $R^{P11}$ is independently selected from cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$a)lkyloxy, cyanoalkoxy, cyanocycloalkyloxy, cycloalkyloxy, oxo, heterocyclyl, —$NR^{hh}R^h$, ($NR^{hh}R^h$)alkyl, ($NR^{hh}R^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, ($NR^hR^h$)sulfonyl, heteroarylsulfonyl, —$S(=O)_2R^h$, —$C(=O)R^h$, —$C(=O)NR^hR^h$; and the remaining $R^{P11}$ are independently selected from $R^{P5}$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1, 2, 3, or 4;
pn is 0, 1, or 2;
each $P^2$ is independently:

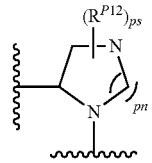

wherein:
each $R^{P12}$ is independently selected from $R^{P5}$, $R^{P11}$, —$C(=O)OR^h$, cyano, alkylsulfonyl, arylsulfonyl, ($NR^hR^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, ($NR^hR^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

ps is 1,2,3, or 4;
pn is 0, 1, or 2;
each $P^3$ is independently a ring of the formula:

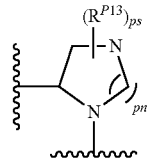

wherein:
the ring is substituted with one or more oxo group;
each $R^{P13}$ is independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;
ps is 0, 1, 2, 3, or 4;
pn is 0, 1, or 2;
each $P^4$ is independently a ring of the formula:

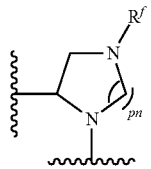

wherein:
the ring is optionally substituted with one or more groups $R^{P14}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups $R^{P14}$ that are attached to the same carbon when taken together with the carbon to which they are attached can form a 3-6 membered carbocyclic or heterocyclic ring;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^5$ is independently a ring of the formula:

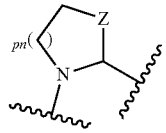

wherein:
the ring is optionally substituted with one or more groups $R^{P15}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups; and where two groups $R^{P10}$ that are attached to the same carbon when taken together with the carbon to which they are attached can form a 3-6 membered carbocyclic or heterocyclic ring;
pn is 0, 1, or 2;
Z is O, S, S(=O), S(=O)$_2$, or NR$^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $P^6$ is independently a ring of the formula:

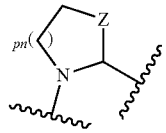

wherein:
the ring is substituted with one or more oxo and is optionally substituted with one or more groups $R^{P16}$ that are independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
Z is O, S, S(=O), S(=O)$_2$, or NR$^f$;
pn is 0, 1, or 2;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;

each $P^7$ is a bridged 5-15 membered bicyclic heterocyclic ring that is attached to the remainder of the compound of formula II through one N-link and through one C-link; wherein the ring is optionally substituted with one or more groups independently selected from $R^{P6}$ and $R^{P11}$;

each $P^8$ is independently a ring of the formula:

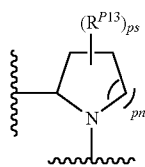

wherein:
ps is 2, 3, 4, 5, or 6;
pn is 0, 1 or 2;
each $R^{P13}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups; where in at least one case two groups $R^{P13}$ that are attached to the same carbon are taken together with the carbon to which they are attached and form a 4-6 membered heterocyclic ring;

each $P^{10}$ is independently:

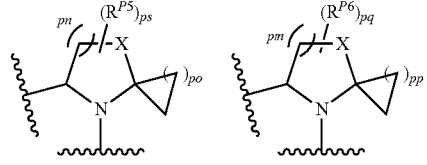

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;
pm and pn are independently 0, 1, or 2;
po and pp are independently 1, 2, or 3;
each $P^{11}$ is independently:

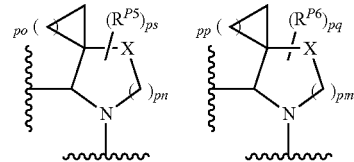

wherein:
X is selected from O, S, S(O), SO$_2$, CH$_2$, CHR$^{P10}$, and C(R$^{P10}$)$_2$; provided that when pn or pm is 0, X is selected from CH$_2$, CHR$^{P10}$, and C(R$^{P10}$)$_2$;
each $R^{P10}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
each $R^{P5}$ and $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;

pq and ps are independently 0, 1, 2, 3, or 4;
pm and pn are independently 0, 1, or 2;
po and pp are independently 1, 2, or 3;
each $P^{12}$ is independently:

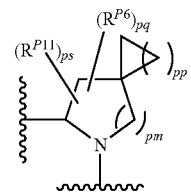

wherein:
each $R^{P6}$ is independently selected from alkoxy, alkyl, aryl, halo, haloalkyl, hydroxy, and —$NR^{Pa}R^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
pp is independently 1, 2, or 3;
ps is 1, 2, 3, or 4;

$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^{hh}$R$^h$)alkyl, (NR$^h$R$^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$; and the remaining $R^{P11}$ are independently selected from $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{13}$ is independently:

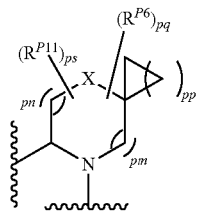

wherein:
X is selected from O, S, S(O), SO$_2$, or NR$^h$;
each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm and pn are independently 0, 1, or 2 but the sum of pn and pm is greater than zero;
pp are independently 1, 2, or 3;
ps is 1, 2, 3, or 4;
each $R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl, —NR$^{hh}$R$^h$, (NR$^h$R$^h$)alkyl, (NR$^h$R$^h$)carbonyl, wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring; wherein each $R^{hh}$ is independently aryl, arylalkyl, heterocycle, heterocyclyoxy, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, (NR$^h$R$^h$)sulfonyl, heteroarylsulfonyl, —S(=O)$_2$R$^h$, —C(=O)R$^h$, —C(=O)NR$^h$R$^h$, $R^{P5}$, cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy, aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; and when two $R^h$ groups are present then they may come together with the atoms to which they are bound to form a 4-15 membered heterocyclic ring;

each $P^{14}$ is independently:

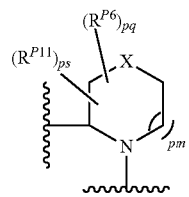

wherein:
the ring is substituted with one or more oxo group;
X is NR$^f$;
each $R^f$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl, —S(=O)$_2$NR$^h$R$^h$, —S(=O)$_2$R$^h$, C(=O)R$^h$, C(=O)OR$^h$, —C(=O)NR$^h$R$^h$; each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, sulfonylalkyl; or when two $R^h$ groups are present then they may come together with the atoms to which they are bound to form a 4-15 membered heterocyclic ring;
each $R^{P6}$ is independently selected from alkoxy, alkyl, aryl, halo, haloalkyl, hydroxy, and —NR$^{Pa}$R$^{Pb}$, wherein the alkyl can optionally form a fused three- to six-membered ring with an adjacent carbon atom, wherein the three- to six-membered ring is optionally substituted with one or two alkyl groups;
pq is independently 0, 1, 2, 3, or 4;
pm is independently 0, 1, or 2;
ps is 1, 2, 3, or 4;
$R^{P11}$ is independently selected from cyano, alkylsulfonyl, arylsulfonyl, (NR$^h$R$^h$)sulfonyl, heterocyclylsulfonyl, heteroarylsulfonyl, haloalkoxy, alkoxyalkyloxy, haloalkoxyalkyloxy, cycloalkyoxyalkyloxy aryloxyalkyloxy, heteroaryloxyakyloxy, heterocyclooxyalkyloxy, (NR$^h$R$^h$)alkyloxy, cyanoalkoxy, cyanocycloalkyloxy, cycloalkyloxy, oxo, heterocyclyl; wherein each $R^h$ is independently —H, alkyl, alkoxyamino, aryl, arylalkyl, heterocycle, heterocyclyoxy, alkenyl, alkenyloxy, alkynyl, alkoxyalkyl, haloalkyl, cyanoalkyl, haloalkoxyalkyl, aminoalkyl, alkylaminoalkyl, dialkylaminoalkyl, or sulfonylalkyl; and when two $R^h$ groups are present then they may come together with the atoms to which they are bound to form a 4-15 membered heterocyclic ring;

each $P^{15}$ is:

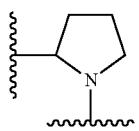

which is substituted with one or two groups independently selected from alkoxyalkyl, haloalkoxyalkyl, alkylsulfanyl, alkylsulfanylalkyl, cyanoalkyl, and cycloalkylalkyl.

each $P^{16}$ is:

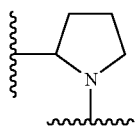 [SMILES: *C1CCCN1*]

which is substituted with methylene;

each $P^{17}$ is:

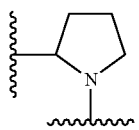 [SMILES: *C1CCCN1*]

which is substituted with one or two groups independently selected from alkenyl, alkynyl, cycloalkyl, cycloalkylalkenyl, and cycloalkylalkynyl.

each $P^{18}$ is:

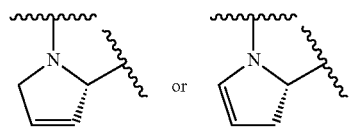

which is optionally substituted with one or two groups independently selected from halo, alkyl, alkoxyalkyl, haloalkyl, cycloalkyl, and cycloalkylalkyl;

each $P^{19}$ is:

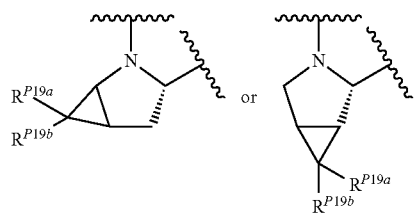

wherein each $R^{P19a}$ is independently selected from H and halo; and each $R^{P19b}$ is independently selected from halo;

each —$Z^0$— is —C(=O)— or —C(=S)—;

each —$Z^1$— is independently a bond, or —C($R^{Z1}$)$_2$—; wherein each $R^{Z1}$ is independently H, alkyl, haloalkyl, or halo;

each —$Z^2$— is independently saturated or partially unsaturated ($C_3$-$C_8$)cycloalkyl that is optionally substituted with one or more groups independently selected from $R^{41}$ and $R^{43}$;

each —$Z^3$— is independently saturated, partially unsaturated, or aromatic 4-8 membered heterocyclic or heteroaryl ring that is optionally substituted with one or more groups independently selected from $R^{41}$ and $R^{43}$;

each —$Z^4$— is independently:

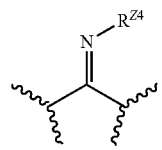

wherein each $R^4$ is independently H, alkyl, cyano, aryl, or heteroaryl;

each —$Z^5$— is independently:

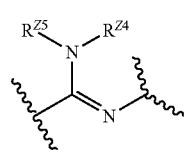

wherein each $R^{Z5}$ is independently H, alkyl, cyano, aryl, or heteroaryl; or two $R^{Z5}$s together with the nitrogen to which they are attached form a 4-8 membered heterocyclic ring that is optionally substituted with one or more oxo and with one or more groups independently selected from $R^{41}$ and $R^{43}$;

each —$Z^6$— is independently —C($R^{Z1}$)— and is double bonded to a carbocyclic P; wherein $R^{Z1}$ is independently H, alkyl, haloalkyl, or halo;

each $E^0$ is independently —N$R^{Ec}R^{Ed}$ wherein $R^{Ec}$ and $R^{Ed}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, (N$R^eR^f$)alkyl, ($NR^eR^f$)alkylcarbonyl, ($NR^eR^f$)carbonyl, ($NR^eR^f$) sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro;

each E is independently —OC(=O)$NR^{Ee}R^{Ef}$ wherein each $R^{Ee}$ and $R^{Ef}$ are each independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$) sulfonyl, —C(NCN)OR', and —C(NCN)$NR^XR^Y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro; or wherein $R^{Ee}$ and $R^{Ef}$, together with the nitrogen atom to which they are attached, form a heterocycle;

each E2 is independently —$NR^aR^b$, wherein $R^a$ is haloalkyl and $R^b$ is H, alkyl, alkoxycarbonyl. or haloalkyl;

each E3 is independently —$NR^{Ec}R^{E3a}$, wherein $R^{E3a}$ is ($C_3$-$C_6$)cycloalkyloxycarbonyl;

each E4 is independently —OC(=O)$OR^{E4a}$, wherein $R^{E4a}$ is cycloalkyl, aryl, or alkyl;

each E5 is independently —$NR^{Ec}S$(=O)$_2OR^{E5a}$, wherein $R^{E5a}$ is cycloalkyl, aryl or alkyl;

each E6 is independently —$NR^{Ec}S$(=O)$_2R^{E6a}$, wherein $R^{E6a}$ is cycloalkyl, aryl, or alkyl;

each $E^7$ is independently —$NR^{Ec}OR^{E7a}$, wherein $R^{E7a}$ is cycloalkyl, aryl, alkyl, haloalkyl, cycloalkylalkyl or heteroaryl;

each $V^0$ is independently H, alkyl, arylalkyl, alkenyl, CO, cycloalkylalkyl, cycloalkyl, alkoxyalkyl, alkoxyalkylcarbonylalkyl, alkoxycarbonylalkyl, alkylsulfanylalkyl, aryloxyalkylcarbonylalkyl, carboxyalkyl, heterocyclylalkyl, heterocyclylcarbonylalkyl, hydroxyalkyl, NRRCOalkyl, wherein each R is independently selected from hydrogen and alkyl;

and where in arylalkyl the alkyl can be substituted with up to three aryl groups, and the alkyl part of the arylalkyl is further optionally substituted with one or two additional groups independently selected from alkoxy, alkyocarbonyloxy, halo, haloalkoxy, haloalkyl, heterocyclyl, hydroxy;

and the aryl part can be substituted with 1, 2, 3, 4, or 5 substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^XR^Y$, —($NR^XR^Y$)alkyl, oxo, and —P(O)$OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

and the heterocyclyl can be substituted with 1, 2, 3, 4, or 5 substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —$NR^XR^Y$, ($NR^XR^Y$)alkyl, and oxo, wherein the alkyl part of the arylalkyl and the heterocyclylalkyl are unsubstituted and wherein the aryl, the aryl part of the arylalkyl; the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro;

each $V^1$ is independently cyanoalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^2$ is independently haloalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; $R^{Va}$ and $R^{Vb}$ are each independently selected from hydrogen, alkenyl, and alkyl;

each $V^3$ is independently alkyl, which is substituted with one or more oxo, and which is optionally substituted with one or more groups independently selected from cycloalkyl, halo, aryl, alkenyl, and cyano;

each $V^4$ is independently haloalkoxyalkyl, which is optionally substituted with one or more groups independently selected from cycloalkyl, alkoxy, haloalkoxy, cycloalkenyl, heterocycle, heteroaryl, hydroxy, and $NR^{Va}R^{Vb}$C(=O)O—; wherein $R^{Va}$ and $R^{Vb}$ are each independently selected from hydrogen, alkenyl, and alkyl;

each $V^5$ is independently alkylsulfonylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^6$ is independently arylsulfonylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^7$ is independently heterocyclosulfonylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^8$ is independently spirocycloalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^9$ is independently spirocycloalkylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{10}$ is independently fused bicycliccycloalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{11}$ is independently fused bicycliccycloalkylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{12}$ is independently bridged-bicycliccycloalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{13}$ is independently bridged-bicyclic-cycloalkylalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{14}$ is independently aryloxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{15}$ is independently arylalkoxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{16}$ is independently cycloalkyloxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{17}$ is independently cycloalkylalkyloxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V is independently heterocyclooxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{19}$ is independently heterocycloalkyloxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V is independently heteroaryloxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V$^{21}$ is independently heteroarylalkyloxyalkyl, which is optionally substituted with one or more groups independently selected from cycloalkyl, alkoxy, haloalkoxy, cycloalkenyl, heterocycle, heteroaryl, hydroxy, and NR$^{Va}$R$^{Vb}$C(=O)O—; R$^{Va}$ and R$^{Vb}$ are each independently selected from hydrogen, alkenyl, and alkyl;

each V is independently cycloalkenylalkyl;

each V$^{23}$ is independently arylalkyl, wherein the aryl is substituted with one or more groups independently selected from cycloalkyl, alkenyl, cycloalkylalkyl, cyanoalkyl, cycloalkoxy, hydroxyalkoxy, —C(=O)NR$^X$R$^Y$, S(=O)$_2$NR$^X$R$^Y$, alkylsulfanyl, alkylsulfonyl, haloalkylsulfanyl, haloalkylsulfonyl, alkylsulfonylalkyl, alkylsulfonylalkyl, arylsulfanyl, arylsulfonyl, alkoxyalkoxy, alkynyl, aryloxy, heteroaryloxy, alkylsulfonylamino;

R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^{Y'}$)carbonyl, wherein R$^{X'}$ and R$^{Y'}$ are independently selected from hydrogen and alkyl;

each V is independently heterocycloalkyl, wherein the heterocycle is substituted with one or more groups independently selected from cycloalkyl, alkenyl, cycloalkylalkyl, cyanoalkyl, cycloalkoxy, hydroxyalkoxy, —C(=O)NR$^X$R$^Y$, S(=O)$_2$NR$^X$R$^Y$, alkylsulfanyl, alkylsulfonyl, haloalkylsulfanyl, haloalkylsulfonyl, alkylsulfonylalkyl, alkylsulfonylalkyl, arylsulfanyl, arylsulfonyl, alkoxyalkyoxy, alkynyl, aryloxy, heteroaryloxy, alkylfulfonylamino;

R$^X$ and R$^Y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and (NR$^{X'}$R$^Y$)carbonyl, wherein R$^{X'}$ and R$^{Y'}$ are independently selected from hydrogen and alkyl;

each T$^1$ is independently a spiro, branched or fused bicycloalkyl;

each T$^2$ is independently aryl;

each T$^3$ is independently heteroaryl;

each T$^4$ is independently arylalkyl;

each T$^5$ is independently haloalkyl;

each T$^6$ is independently heteroarylalkyl;

each T$^7$ is independently heterocycle; and each T$^8$ is independently heterocycloalkyl;

or a pharmaceutically acceptable salt, or prodrug thereof.

In one embodiment, the compound of Formula I is Formula Ia:

wherein:

Ia

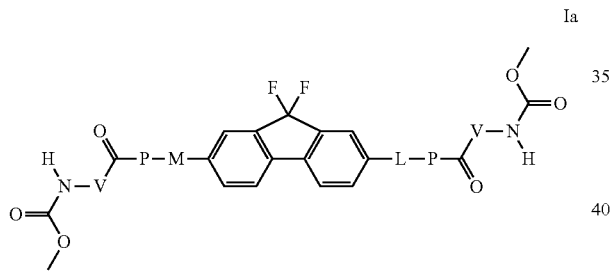

each V is independently alkyl;

L is benzimidazolyl;

M is a 5-membered heteroaryl ring;

each P is independently selected from:

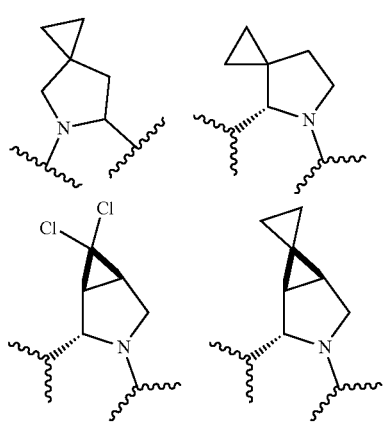

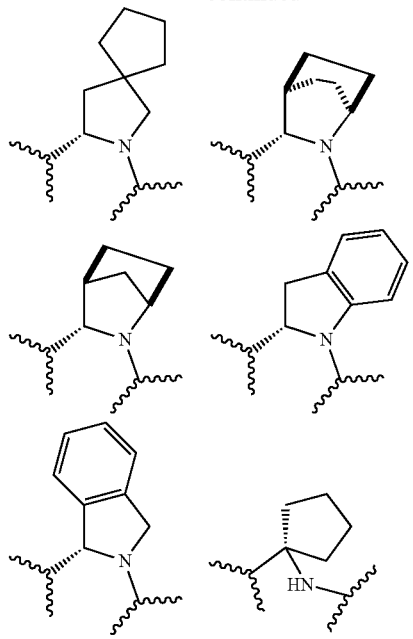

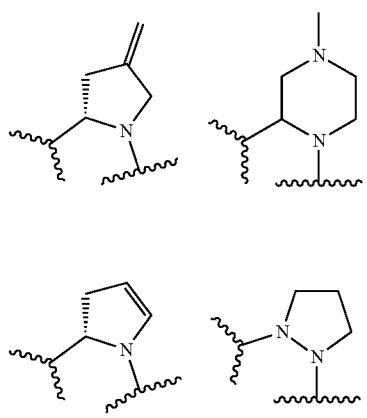

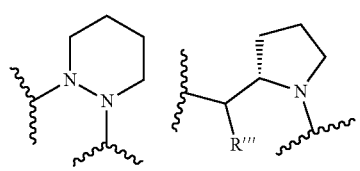

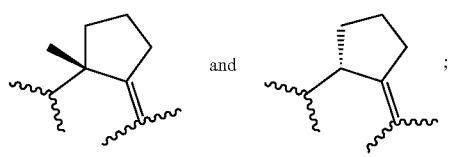

and

R''' is hydrogen or methyl; or a pharmaceutically acceptable salt, or prodrug thereof.

In one embodiment, the compound of Formula I or Ia is:

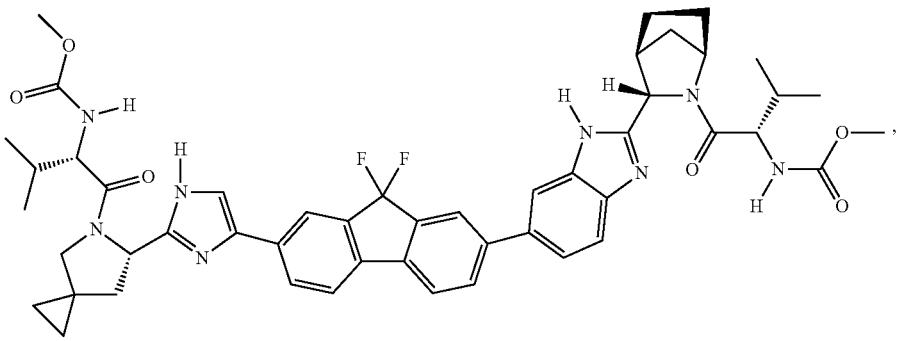

or a pharmaceutically acceptable salt thereof. This compound is also known as ledipasvir.

In one embodiment, the NS5A inhibitor is a compound described in PCT Publication No. WO2013/075029, which is hereby incorporated by reference in its entirety. In one embodiment, the NS5A inhibitor is a compound of Formula II:

$$E^{1a}\text{-}V^{1a}\text{—}C(\!=\!O)\text{—}P^{1a}\text{—}W^{1a}\text{—}P^{1b}\text{—}C(\!=\!O)\text{—}V^{1b}\text{-}E^{1b} \quad \text{II}$$

wherein $W^{1a}$ is

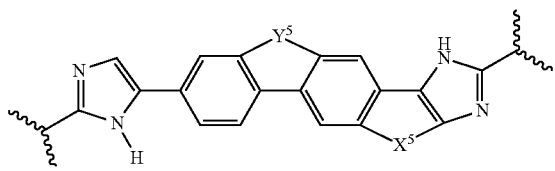

and $W^{1a}$ is optionally substituted with one or more groups independently selected from halo, alkyl, haloalkyl, or cyano;

$Y^5$ is —O—CH$_2$—, or —CH$_2$—O—;

$X^5$ is —CH$_2$—CH$_2$— or —CH=CH—;

$E^{1a}$ is —N(H)(alkoxycarbonyl), —N(H)(cycloalkylcarbonyl) or —N(H)(cycloalkyloxycarbonyl); or $E^{1a}$-$V^{1a}$ taken together are $R^{9a}$;

$E^{1b}$ is —N(H)(alkoxycarbonyl), —N(H)(cycloalkylcarbonyl) or —N(H)(cycloalkyloxycarbonyl); or $E^{1b}$-$V^{1b}$ taken together are $R^{9b}$;

$V^{1a}$ and $V^{1b}$ are each independently selected from:

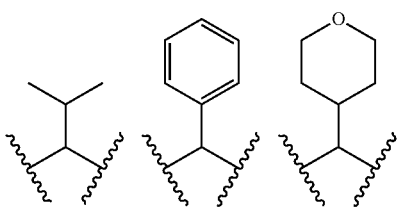

-continued

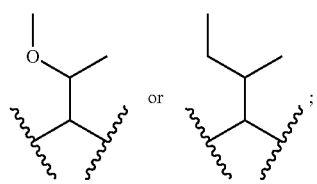

$P^{1a}$ is selected from:

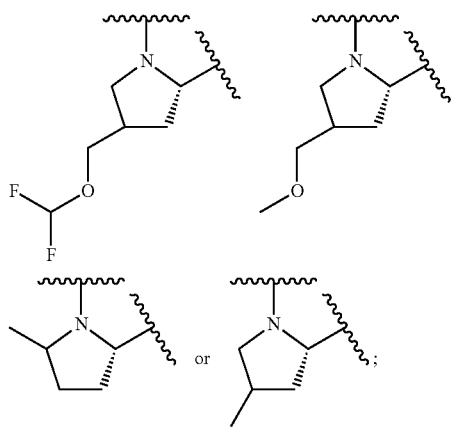

$P^{1b}$ is selected from:

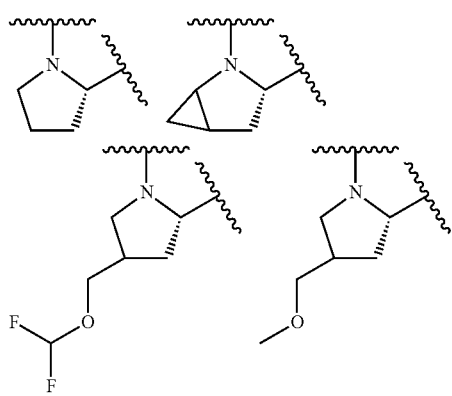

-continued

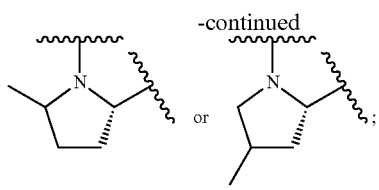

and
$R^{9a}$ and $R^{9b}$ are each independently:

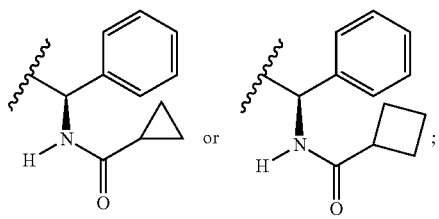 [SMILES: *[C@H](NC(=O)C1CC1)c1ccccc1 ; *[C@H](NC(=O)C1CCC1)c1ccccc1]

or a pharmaceutically acceptable salt or prodrug thereof.

In one embodiment, the compound of Formula II is:

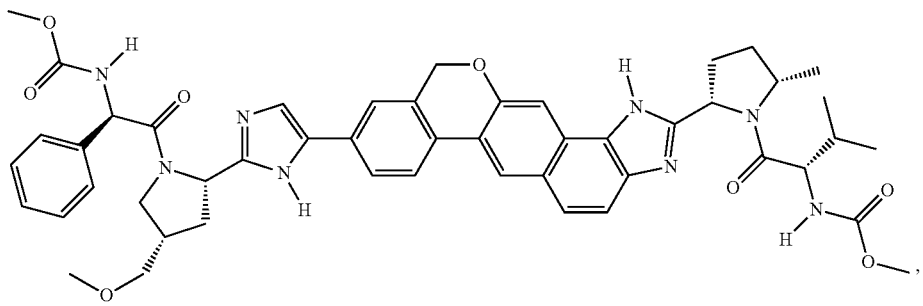

or a pharmaceutically acceptable salt thereof. This compound is also known as velpatasvir.

B. NS5B Inhibitors

In one embodiment, the NS5B inhibitor are compounds found in PCT Publication No. WO2008/121634, which is incorporated by reference in its entirety. Additional NS5B inhibitors may be found in U.S. Pat. No. 7,429,572, WO 2011/123645, WO 2010/135569, U.S. Pat. Nos. 8,841,275, 8,716,262, 8,551,973, 8,173,621, all of which are incorporated by reference in their entirety. In one embodiment, the NS5B inhibitor is a compound of Formula III (described in WO2008/121634):

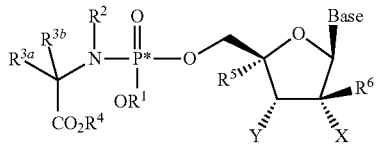

III wherein
(a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —N($R^{1'}$)$_2$, $C_{1-6}$ acylamino, —NHSO$_2C_{1-6}$ alkyl, —SO$_2$($R^{1'}$)$_2$, COR$^{1''}$, and —SO$_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —N($R^{1'}$)$_2$);

(b) $R^2$ is hydrogen, $C_{1-10}$ alkyl, $R^{3a}$ or $R^{3b}$ and $R^2$ together are (CH$_2$)$_n$ so as to form a cyclic ring that includes the adjoining N and C atoms, C(O)CR$^{3a}$R$^{3b}$NHR$^1$, where n is 2 to 4 and $R^1$, $R^{3a}$, and $R^{3b}$;

(c) $R^{3a}$ and $R^{3b}$ are (i) independently selected from hydrogen, $C_{1-10}$ alkyl, cycloalkyl, —(CH$_2$)$_c$(NR$^3$)$_2$, $C_{1-6}$ hydroxyalkyl, —CH$_2$SH, —(CH$_2$)$_2$S(O)$_d$Me, —(CH$_2$)$_3$NHC(=NH)NH$_2$, (1H-indol-3-yl)methyl, (1H-imidazol-4-yl)methyl, —(CH$_2$)$_e$COR$^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are (CH$_2$)$_f$ so as to form a spiro ring; (iv) $R^{3a}$ is hydrogen and $R^{3b}$ and $R^2$ together are (CH$_2$)$_n$ so as to form a cyclic ring that includes the adjoining N and C atoms (v) $R^{3b}$ is hydrogen and $R^{3a}$ and $R^2$ together are (CH$_2$)$_n$ so as to form a cyclic ring that includes the adjoining N and C atoms, where c is 1 to 6, d is 0 to 2, e is 0 to 3, f is 2 to 5, n is 2 to 4, and where $R^3$ is independently hydrogen or $C_{1-6}$ alkyl and $R^3$ is —OR' or —N($R^3$)$_2$);

(vi) $R^{3a}$ is H and $R^{3b}$ is H, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH) NH$_2$, CH$_2$-imidazol-4-yl, CH$_2$OH, CH(OH)CH$_3$, CH$_2$((4'-OH)-Ph), CH$_2$SH, or lower cycloalkyl; or (viii) $R^{3a}$ is CH$_3$, —CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH) NH$_2$, CH$_2$-imidazol-4-yl, CH$_2$OH, CH(OH)CH$_3$, CH$_2$((4'-OH)-Ph), CH$_2$SH, or lower cycloalkyl and $R^{3b}$ is H, where $R^3$ is independently hydrogen or alkyl, which includes, but is not limited to, $C_{1-20}$ alkyl, $C_{1-10}$ alkyl, or $C_{1-6}$ alkyl, $R^3$ is —OR' or —N($R^3$)$_2$);

(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —(CH$_2$)$_p$OH, where p is 1-6, including hydroxyl methyl (CH$_2$OH), CH$_2$F, N$_3$, CH$_2$CN, CH$_2$NH$_2$, CH$_2$NHCH$_3$, CH$_2$N(CH$_3$)$_2$, alkyne (optionally substituted), or halogen, including F, Cl, Br, or I, with the provisos that when X is OH, base is cytosine and $R^6$ is H, $R^5$ cannot be N$_3$ and when X is OH, $R^6$ is CH$_3$ or CH$_2$F and B is a purine base, $R^5$ cannot be H;

(f) $R^6$ is H, CH$_3$, CH$_2$F, CHF$_2$, CF$_3$, F, or CN;

(g) X is H, OH, F, OMe, halogen, NH$_2$, or N$_3$;

(h) Y is OH, H, C$_{1-4}$ alkyl, C$_{2-4}$ alkenyl, C$_{2-4}$ alkynyl, vinyl, N$_3$, CN, Cl, Br, F, I, NO$_2$, OC(O)O(C$_{1-4}$ alkyl), OC(O)O(C$_{1-4}$ alkyl), OC(O)O(C$_{1-4}$ alkenyl), OC(O)O (C$_{2-4}$ alkenyl), OC$_{1-10}$ haloalkyl, O(aminoacyl), O(C$_{1-10}$ acyl), O(C$_{1-4}$ alkyl), O(C$_{2-4}$ alkenyl), S(C$_{1-4}$ acyl), S(C$_{1-4}$ alkyl), S(C$_{2-4}$ alkynyl), S(C$_{2-4}$ alkenyl), SO(C$_{1-4}$ acyl), SO(C$_{1-4}$ alkyl), SO(C$_{2-4}$ alkynyl), SO(C$_{2-4}$ alkenyl), SO$_2$(C$_{1-4}$ acyl), SO$_2$(C$_{1-4}$ alkyl), SO$_2$(C$_{2-4}$ alkynyl), SO$_2$(C$_{2-4}$ alkenyl), OS(O)$_2$(C$_{1-4}$ acyl), OS(O)$_2$(C$_{1-4}$ alkyl), OS(O)$_2$(C$_{2-4}$ alkenyl), NH$_2$, NH(C$_{1-4}$ alkyl), NH(C$_{2-4}$ alkenyl), NH(C$_{2-4}$ alkynyl), NH(C$_{1-4}$ acyl), N(C$_{1-4}$ alkyl)$_2$, N(C$_{1-18}$ acyl)$_2$, wherein alkyl, alkynyl, alkenyl and vinyl are optionally substituted by N$_3$, CN, one to three halogen (Cl, Br, F, I), NO$_2$, C(O)O(C$_{1-4}$ alkyl), C(O)O(C$_{1-4}$ alkyl), C(O)O (C$_{1-4}$ alkynyl), C(O)O(C$_{2-4}$ alkenyl), O(C$_{1-4}$ acyl), O(C$_{1-4}$ alkyl), O(C$_{2-4}$ alkenyl), S(C$_{1-4}$ acyl), S(C$_{1-4}$ alkyl), S(C$_{2-4}$ alkynyl), S(C$_{2-4}$ alkenyl), SO(C$_{1-4}$ acyl), SO(C$_{1-4}$ alkyl), SO(C$_{2-4}$ alkynyl), SO(C$_{2-4}$ alkenyl), SO$_2$(C$_{1-4}$ acyl), SO$_2$(C$_{1-4}$ alkyl), SO$_2$(C$_{2-4}$ alkynyl), SO$_2$(C$_{2-4}$ alkenyl), OS(O)$_2$(C$_{1-4}$ acyl), OS(O)$_2$(C$_{1-4}$ alkyl), OS(O)$_2$(C$_{2-4}$ alkenyl), NH$_2$, NH(C$_{1-4}$ alkyl), NH(C$_{2-4}$ alkenyl), NH(C$_{2-4}$ alkynyl), NH(C$_{1-4}$ acyl), N(C$_{1-4}$ alkyl)$_2$, N(C$_{1-4}$ acyl)$_2$;

the base is a naturally occurring or modified purine or pyrimidine base represented by the following structures:

a
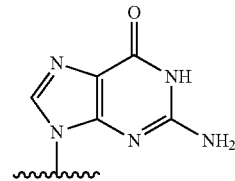

b
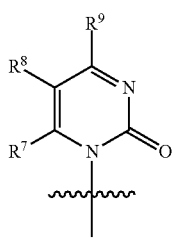

c
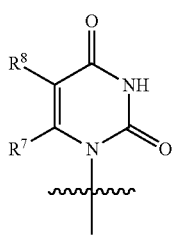

d
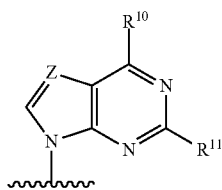

wherein

Z is N or CR$^{12}$;

$R^7$, $R^8$, $R^9$, $R^{10}$, and R" are independently H, F, Cl, Br, I, OH, OR', SH, SR', NH$_2$, NHR', NR'$_2$, lower alkyl of C$_1$-C$_6$, halogenated (F, Cl, Br, I) lower alkyl of C$_1$-C$_6$, lower alkenyl of C$_2$-C$_6$, halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH═CHCO$_2$H, or CH═CHCO$_2$R', wherein R' is an optionally substituted alkyl, which includes, but is not limited to, an optionally substituted C$_{1-20}$ alkyl, an optionally substituted C$_{1-10}$ alkyl, an optionally substituted lower alkyl; an optionally substituted cycloalkyl; an optionally substituted alkynyl of C$_2$-C$_6$, an optionally substituted lower alkenyl of C$_2$-C$_6$, or optionally substituted acyl, which includes but is not limited to C(O) alkyl, C(O)(C$_{1-20}$ alkyl), C(O)(C$_{1-10}$ alkyl), or C(O)(lower alkyl) or alternatively, in the instance of NR'$_2$, each R' comprise at least one C atom that are joined to form a heterocycle comprising at least two carbon atoms; and $R^{12}$ is H, halogen (including F, Cl, Br, I), OH, OR', SH, SR', NH$_2$, NHR', NR'$_2$, NO$_2$, lower alkyl of C$_1$-C$_6$, halogenated (F, Cl, Br, I) lower alkyl of C$_1$-C$_6$, lower alkenyl of C$_2$-C$_6$, halogenated (F, Cl, Br, I) lower alkenyl of C$_2$-C$_6$, lower alkynyl of C$_2$-C$_6$, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH═CHCO$_2$H, or CH═CHCO$_2$R'; with the proviso that when base is represented by the structure c with $R^{11}$ being hydrogen, $R^{12}$ is not a: (i) —C≡C—H, (ii) —C≡CH$_2$, or (iii) —NO$_2$.

In one embodiment, the compound of Formula III is:

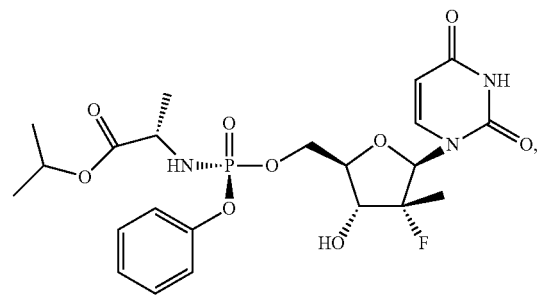 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

or a pharmaceutically acceptable salt, or diastereomer or a mixture of diastereomer thereof.

In one embodiment, the NS5B inhibitor is sofosbuvir.

In another embodiment, the NS5B inhibitor is mericitabine or other compounds described in PCT Publication No. WO2007/065829, which is incorporated herein by reference.

C. NS3 Inhibitors

In one embodiment, the NS3 inhibitor are compounds found in PCT Publication No. WO 2014/008285, which is incorporated by reference in its entirety. Additional NS3 inhibitors may be found in WO 2006/020276, WO 2007/009109, WO 2008/005565, WO 2009/005676, WO 2009/005677, and WO 2014/008285, all of which are incorporated by reference in their entirety. In one embodiment, the NS3 inhibitor is a compound of Formula IV (described in WO 2014/008285):

IV or a stereoisomer, or a mixture of stereoisomers, or a pharmaceutically acceptable salt thereof, wherein:

J is $J^1$, $J^2$, $J^3$, $J^4$, $J^5$, $J^6$, $J^7$, $J^8$ or $J^9$;

⊙ is $T^1$, $T^2$, $T^3$, $T^4$, $T^5$, $T^6$, $T^7$, $T^8$, $T^9$, $T^{10}$, $T^{11}$, $T^{12}$, $T^{13}$ or $T^{14}$;

L is $L^1$, $L^2$, $L^3$, $L^4$, $L^5$, $L^6$, $L^7$, $L^8$, $L^9$ or $L^{10}$;

X is —O—, —CH$_2$—, —OC(O)—, —C(O)O—, —C(O)—, —SO$_2$—, —S(O)—, —N(R$^{16}$)—, —S—, =N—O— or a bond;

A is —C(O)—, —S(O)$_2$—, a 6-10 membered arylene, 5-10 membered heteroarylene, or 4-10 membered heterocyclene, wherein any of said arylene, heterocyclene, or heteroarylene is optionally substituted with 1-4 $Z^1$ groups;

M is a bond, $C_1$-$C_6$ alkylene, —O—, or —N(R$^{16}$)—;

$R^1$ is H or F;

$R^3$, $R^4$, and $R^5$ are each independently selected from H or $Z^1$;

Q is $Q^1$, $Q^2$, $Q^3$, $Q^4$, $Q^5$, $Q^6$ or $Q^7$;

E is $E^1$, $E^2$, $E^3$, $E^4$, $E^5$, or $E^6$;

G is —CO$_2$H, —CONHSO$_2$Z$^2$, tetrazolyl, —CONHP(O)(R$^{16}$)$_2$, —P(O)(OH)(R$^{16}$), and —P(O)(R$^{16}$)$_2$;

☺ is $U^1$, $U^2$, $U^3$, $U^4$, $U^5$, $U^6$ or $U^7$;

$J^1$ is halogen;

$J^2$ is —OH and $R^1$ is H;

$J^3$ is —NR$^{17}$R$^{18}$ and $R^1$ is H;

$J^4$ is $C_1$-$C_8$ alkyl;

$J^5$ is $C_1$-$C_8$ alkyl substituted with 1-4 $Z^3$ groups;

$J^6$ is $C_3$-$C_8$ carbocyclyl optionally substituted with 1-4 $Z^3$ groups;

$J^7$ is $C_6$-$C_{10}$ aryl, 5-10 membered heteroaryl, or 4-10 membered heterocyclyl optionally substituted with 1-4 $Z^3$ groups;

$J^8$ is $C_1$-$C_8$ alkoxy optionally substituted with 1-4 $Z^3$ groups and $R^1$ is H;

$J^9$ is $C_3$-$C_8$ carbocyclyloxy optionally substituted with 1-4 $Z^3$ groups and $R^1$ is H;

$T^1$ is $C_3$-$C_8$ carbocyclylene that is attached to L and M through two adjacent carbons;

$T^2$ is $C_3$-$C_8$ carcbocyclene that is attached to L and M through two adjacent carbons, wherein said carbocyclylene is substituted with 1-4 $C_1$-$C_8$ alkyl groups;

$T^3$ is $C_3$-$C_8$ carcbocyclene that is attached to L and M through two adjacent carbons, wherein said carbocyclylene is substituted with 1-4 halogen atoms and said carbocyclylene is optionally substituted with 1-4 $C_1$-$C_6$ alkyl groups;

$T^4$ is $C_3$-$C_8$ carbocyclene that is attached to L and M through two adjacent carbons, wherein said carbocyclylene is optionally substituted with a $C_1$-$C_8$ alkyl group, wherein said alkyl group is optionally substituted with 1-4 $Z^3$ groups;

$T^5$ is 4-10 membered heterocyclene that is attached to L and M through two adjacent carbons;

$T^6$ is 4-10 membered heterocyclene that is attached to L through a carbon atom and attached to M through an N atom, wherein said heterocyclene is optionally substituted with 1-4 $Z^1$ groups;

$T^7$ is 4-10 membered heterocyclene that is attached to M through a carbon atom and attached to L through an N atom, wherein said heterocyclene is optionally substituted with 1-4 $Z^1$ groups;

$T^8$ is 4-10 membered heterocyclene that is attached to L and M through two adjacent carbons, wherein said heterocyclene is optionally substituted with 1-4 $Z^1$ groups;

$T^9$ is $C_5$-$C_{12}$ spiro bicyclic carbocyclylene that is attached to L and M through two adjacent carbons, wherein said spiro bicyclic carbocyclylene is optionally substituted with 1-4 $Z^1$ groups;

$T^{10}$ is $C_5$-$C_{12}$ fused bicyclic carbocyclylene that is attached to L and M through two adjacent carbons, wherein said fused bicyclic carbocyclylene is optionally substituted with 1-4 $Z^1$ groups;

$T^{11}$ is $C_5$-$C_{12}$ bridged bicyclic carbocyclylene that is attached to L and M through two adjacent carbons, wherein said bridged bicyclic carbocyclylene is optionally substituted with 1-4 $Z^1$ groups;

$T^{12}$ is $C_4$-$C_8$ carbocylene that is attached to L and M through two non-adjacent carbons, wherein said carcbocyclene is optionally substituted with 1-4 $Z^1$ groups;

$T^{13}$ is a 5-8 membered fused, bridged, or spiro bicyclic heterocyclene that is attached to L and M through two adjacent atoms, wherein said heterocyclene is optionally substituted with 1-4 $Z^1$ groups;

$T^{14}$ is $C_3$-$C_8$ carbocyclylene that is attached to L and M through two adjacent carbons, wherein said carbocyclylene is optionally substituted with 1-4 $Z^4$ groups;

$L^1$ is $C_1$-$C_8$ alkylene or $C_2$-$C_8$ alkenylene;

$L^2$ is $C_1$-$C_8$ alkylene or $C_2$-$C_8$ alkenylene wherein said $C_1$-$C_8$ alkylene is substituted with 1-4 halogens or said $C_2$-$C_8$ alkenylene is substituted with 1-4 halogens;

$L^3$ is $C_1$-$C_8$ alkylene or $C_2$-$C_8$ alkenylene wherein said $C_1$-$C_8$ alkylene is substituted with 1-4 $Z^4$ groups or said $C_2$-$C_8$ alkenylene is substituted with 1-4 $Z^4$ groups and wherein each is optionally substituted with 1-4 halogens;

$L^4$ is $C_1$-$C_8$ alkylene or $C_2$-$C_8$ alkenylene substituted with two geminal $C_3$-$C_4$ alkyl groups that come together to form a spiro $C_3$-$C_8$ carbocyclyl group, wherein $L^4$ is optionally substituted with 1-4 $Z^1$ groups;

$L^5$ is 2-8 membered heteroalkylene or 4-8 membered heteroalkenylene that is connected to ⊙ by an O, S or N atom and said heteroalkylene or heteroalkenylene is optionally substituted with 1-4 $Z^3$ groups;

$L^6$ is 2-8 membered heteroalkylene or 5-8 membered heteroalkenylene that is connected to ⊙ by a carbon atom and said heteroalkylene or heteroalkenylene is substituted with 1-4 halogen atoms and is optionally substituted with 1-4 $Z^4$ groups;

$L^7$ is 2-8 membered heteroalkylene or 4-8 membered heteroalkenylene that is connected to ⊙ by a carbon atom and said heteroalkylene or heteroalkenylene is optionally substituted with 1-4 $Z^4$ groups;

$L^8$ is $L^{8A}$-$L^{8B}$-$L^{8C}$ wherein L and L are each independently selected from $C_1$-$C_6$ alkylene, $C_1$-$C_6$ heteroalkylene, $C_2$-$C_6$ alkenylene or a bond and L is a 3- to 6-membered saturated or unsaturated ring containing 0 to 3 heteroatoms selected from N, O, or S, wherein $L^{8A}$ and $L^{8C}$ connect to $L^{8B}$ at two different ring atoms and $L^{8B}$ is optionally substituted with 1-4 $Z^1$ groups;

$L^9$ is $C_2$-$C_8$ alkynylene optionally substituted with 1-4 $Z^1$ groups;

$L^{10}$ is $C_1$-$C_8$ alkylene or $C_3$-$C_8$ alkenylene substituted with two geminal $Z^1$ groups that come together to form a spiro 4-8 membered heterocyclyl group, wherein $L^{10}$ is optionally substituted with 1-4 $Z^1$ groups;

$U^1$ is $C_6$-$C_{14}$ membered arylene optionally substituted with 1-4 W groups;

$U^2$ is $C_3$-$C_8$ membered carbocyclylene optionally substituted with 1-4 W groups;

$U^3$ is 4-14 membered heterocyclene optionally substituted with 1-4 W groups that are located on one or more ring atoms selected from C or N;

$U^4$ is 5 or 6 membered monocyclic heteroarylene containing 1, 2 or 3 heteroatoms independently selected from N, O, or S, wherein said heteroarylene is optionally substituted with 1-4 W groups that are located on one or more ring atoms selected from C or N;

$U^5$ is 8, 9 or 10 membered fused bicyclic heteroarylene containing 1, 2 or 3 heteroatom ring atoms independently selected from N, O, or S, wherein said heteroarylene is optionally substituted with 1-4 W groups that are located on one or more ring atoms selected from C or N;

$U^6$ is 11-14 membered fused tricyclic heteroarylene containing 1, 2, 3 or 4 heteroatom ring atoms independently selected from N, O, or S, wherein said heteroarylene is optionally substituted with 1-4 W groups that are located on one or more ring atoms selected from C or N;

$U^7$ is 8-10 membered fused bicyclic heteroarylene containing 4 heteroatom ring atoms independently selected from N, O, or S, wherein said heteroaryl is optionally substituted with 1-2 W groups that are located on one or more ring atoms selected from C or N;

W is independently $W^1$, $W^2$, $W^3$, $W^4$, $W^5$, $W^6$ or $W^7$;

$W^1$ is oxo, halogen, —$OR^6$, $C_1$-$C_6$ alkyl, —CN, —$CF_3$, —$SR^6$, —$C(O)_2R^6$, —$C(O)N(R^6)_2$, —$C(O)R^6$, —$N(R^6)C(O)R^6$, —$SO_2(C_1$-$C_6$ alkyl), —$S(O)(C_1$-$C_6$ alkyl), $C_3$-$C_8$ carbocyclyl, $C_3$-$C_8$ cycloalkoxy, $C_1$-$C_6$ haloalkyl, —$N(R^6)_2$, —$NR^6(C_1$-$C_6$ alkyl)$O(C_1$-$C_6$ alkyl), halo($C_1$-$C_6$ alkoxy), —$NR^6SO_2R^6$, —$SO_2N(R^6)_2$, —$NHCOOR^6$, —$NHCONHR^6$, $C_6$-$C_{10}$ aryl, 5-14 membered heteroaryl, 4-10 membered heterocyclyl or —O(4-10 membered heterocyclyl), wherein said $W^1$ alkyl, carbocyclyl, cycloalkoxy, haloalkyl, haloalkoxy, aryl, heteroaryl, or heterocyclyl is optionally substituted with 1-4 $Z^{1c}$ groups;

each $R^6$ is independently selected from H, $C_6$-$C_{10}$ aryl or $C_1$-$C_6$ alkyl, wherein said aryl or alkyl is optionally substituted with 1 to 4 substituents independently selected from halogen atoms, $C_1$-$C_6$ alkyl, $C_6$-$C_{10}$ aryl, $C_3$-$C_8$ carbocyclyl, 5-14 membered heteroaryl, 4-10 membered heterocyclyl, halo($C_1$-$C_6$ alkoxy), —OH, —$O(C_1$-$C_6$ alkyl), —SH, —$S(C_1$-$C_6$ alkyl), —$NH_2$, —$NH(C_1$-$C_6$ alkyl), —$N(C_1$-$C_6$ alkyl)$_2$, —$C(O)(C_1$-$C_6$ alkyl), —$SO_2N(C_1$-$C_6$ alkyl)$_2$, —$NHCOO(C_1$-$C_6$ alkyl), —$NHCO(C_1$-$C_6$ alkyl), —$NHCONH(C_1$-$C_6$ alkyl), —$CO_2(C_1$-$C_6$ alkyl), or —$C(O)N(C_1$-$C_6$ alkyl)$_2$;

$W^2$ is $C_1$-$C_6$ alkoxy substituted with a 5-14 membered heteroaryl or $C_6$-$C_{10}$ aryl; wherein said heteroaryl or aryl is substituted with 1-4 $Z^1$ groups;

$W^3$ is $C_2$-$C_6$ alkynyl substituted with an $C_6$-$C_{10}$ aryl, $C_3$-$C_8$ carbocyclyl, $C_1$-$C_8$ alkyl, $C_1$-$C_6$ haloalkyl, 4-10 membered heterocyclyl, or 5-14 membered heteroaryl; wherein said aryl, carbocyclyl, alkyl, haloalkyl, heterocyclyl, or heteroaryl is optionally substituted with 1-4 $Z^1$ groups;

$W^4$ is —$SF_5$;

$W^5$ is —$O(C_2$-$C_6$ alkyl)$OR^{22}$ wherein $R^{22}$ is an $C_6$-$C_{10}$ aryl, 5-14 membered heteroaryl or 4-10 membered heterocyclyl, and wherein said aryl, heteroaryl or heterocyclyl is optionally substituted with 1-4 $Z^1$ groups;

$W^6$ is —$O(C_2$-$C_6$ alkyl)$NR^{16}R^{22}$ wherein $R^{22}$ is an $C_6$-$C_{10}$ aryl, 5-14 membered heteroaryl or 4-membered heterocyclyl, and wherein said aryl, heteroaryl or heterocyclyl is optionally substituted with 1-4 $Z^1$ groups;

$W^7$ is —O(5-14 membered heteroaryl); wherein said —O(5-14 membered heteroaryl) is optionally substituted with 1-4 $Z^1$ groups;

$E^1$ is $C_2$-$C_6$ alkenyl;

$E^2$ is $C_1$-$C_6$ alkyl;

$E^3$ is $C_1$-$C_6$ haloalkyl;

$E^4$ is $C_2$-$C_6$ haloalkenyl;

$E^5$ is $C_3$-$C_6$ carbocyclyl;

$E^6$ is $C_1$-$C_6$ alkyl substituted with —$OCH_3$, —$OCD_3$, —$OCF_3$, or —$OCF_2H$;

$Q^1$ is H, $C_1$-$C_8$ alkyl, $C_3$-$C_8$ carbocyclyl, $C_6$-$C_{10}$ aryl, 5-6 membered heteroaryl, or 5-6 membered heterocyclyl, wherein when $Q^1$ is not H, said $Q^1$ is optionally substituted with 1-3 substituents independently selected from halogen, —$OR^6$, —$SR^6$, —$N(R^6)_2$, $C_6$-$C_{10}$ aryl, $C_1$-$C_6$ alkyl, $C_1$-$C_6$ haloalkyl, $C_1$-$C_6$ haloalkoxy, —CN, —$CF_3$, —$SO_2(C_1$-$C_6$ alkyl), —$S(O)(C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —$C(O)R^6$, or —$CON(R^6)_2$;

$Q^2$ is $C_5$-$C_{10}$ spiro bicyclic carbocyclyl optionally substituted with 1-4 $Z^1$ groups;

$Q^3$ is $C_5$-$C_{10}$ fused bicyclic carbocyclyl optionally substituted with 1-4 $Z^1$ groups;

$Q^4$ is $C_5$-$C_{10}$ bridged bicyclic carbocyclyl optionally substituted with 1-4 $Z^1$ groups;

$Q^5$ is 4-membered heterocyclyl having 1 heteroatom selected from N, O or S wherein $Q^5$ is optionally substituted with alkyl or 1-4 $Z^3$ groups;

$Q^6$ is $C_1$-$C_8$ alkyl, $C_3$-$C_8$ carbocyclyl, $C_6$-$C_{10}$ aryl, 5-6 membered heteroaryl, or 5-6 membered heterocyclyl, wherein $Q^6$ is substituted with 1 oxo group and with 0 to 3 substituents independently selected from halogen, —$OR^6$, —$SR^6$, —$N(R^6)_2$, $C_6$-$C_{10}$ aryl, $C_1$-$C_6$ alkyl, $C_1$-$C_6$ haloalkyl, $C_1$-$C_6$ haloalkoxy, —$NO_2$, —CN, —$CF_3$, —$SO_2(C_1$-$C_6$ alkyl), —$S(O)(C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —$C(O)R^6$, or —$CON(R^6)_2$;

$Q^7$ is $C_3$-$C_8$ carbocyclyl, wherein $Q^7$ is substituted with 4-8 F atoms and each carbon of $Q^7$ is substituted with 0-2 F atoms;

each $Z^1$ is independently oxo, halogen, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein any alkyl, alkenyl, alkynyl, carbocyclyl, aryl, heteroaryl or heterocyclyl of $Z^1$ is optionally substituted with 1-4 $Z^{1a}$ groups;

each $Z^{1a}$ is independently oxo, halogen, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)OR$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein any alkenyl, alkynyl, carbocyclyl, aryl, heteroaryl or heterocyclyl of $Z^{1a}$ is optionally substituted with 1-4 $Z^{1c}$ groups;

each $R^{16}$ is independently H, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of $R^{16}$ is optionally substituted with 1-4 $Z^{1c}$ groups;

each $Z^{1c}$ is independently oxo, halogen, $C_1$-$C_8$ alkyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)($C_1$-$C_8$ alkyl), —C(O)O($C_1$-$C_8$ alkyl), —C(O)N($C_1$-$C_8$ alkyl)$_2$, —NH$_2$, —NH($C_1$-$C_8$ alkyl), —N($C_1$-$C_8$ alkyl)$_2$, —NHC(O)O($C_1$-$C_8$ alkyl), —NHC(O)($C_1$-$C_8$ alkyl), —NHC(O)NH($C_1$-$C_8$ alkyl), —OH, —O($C_1$-$C_8$ alkyl), $C_3$-$C_8$ cycloalkoxy, $C_5$-$C_{10}$ bicyclic carbocyclyloxy, —S($C_1$-$C_8$ alkyl) or —S(O)$_2$N($C_1$-$C_8$ alkyl)$_2$ wherein any alkyl, carbocyclyl, aryl, heteroaryl, heterocyclyl or cycloalkoxy portion of $Z^{1c}$ is optionally substituted with 1-4 halogen atoms or $C_1$-$C_6$ alkoxy groups;

$R^{17}$ and $R^{18}$ are each independently H, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, —C(O)R$^{16}$, —C(O)OR$^{16}$, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of R or R is optionally substituted with 1-4 $Z^{1c}$ groups, or $R^{17}$ and $R^{18}$ together with the nitrogen to which they are attached form a 4-7 membered heterocyclyl group, wherein said 4-7 membered heterocyclyl group is optionally substituted with 1-4 $Z^{1c}$ groups;

each $Z^2$ is independently $C_1$-$C_8$ alkyl, $C_3$-$C_8$ carbocyclyl, $C_5$-$C_{10}$ bicyclic carbocyclyl, $C_6$-$C_{10}$ aryl, 5-14 membered heteroaryl, 4-10 membered heterocyclyl, —NR$^{17}$R$^{18}$ or —OR$^{16}$ wherein any alkyl, carbocyclyl, aryl, heteroaryl or heterocyclyl portion of $Z^2$ is optionally substituted with 1-4 $Z^{2a}$ groups;

each $Z^{2a}$ is independently oxo, halogen, $C_1$-$C_8$ alkyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —($C_2$-$C_8$ alkynyl)aryl, —($C_2$-$C_8$ alkynyl)heteroaryl, —CN, —C(O)($C_1$-$C_6$ alkyl), —C(O)O($C_1$-$C_6$ alkyl), —C(O)N($C_1$-$C_6$ alkyl)$_2$, —NH$_2$, —NH($C_1$-$C_6$ alkyl), —N($C_1$-$C_6$ alkyl)$_2$, —NHC(O)O($C_1$-$C_6$ alkyl), —NHC(O)($C_1$-$C_6$ alkyl), —NHC(O)NH($C_1$-$C_6$ alkyl), —OH, —O($C_1$-$C_6$ alkyl), halo($C_1$-$C_6$ alkoxy), $C_3$-$C_8$ cycloalkoxy, —S($C_1$-$C_6$ alkyl), or —SO$_2$N($C_1$-$C_6$ alkyl)$_2$; wherein any alkyl, alkynyl, carbocyclyl, cycloalkoxy, aryl, heteroaryl or heterocyclyl portions of $Z^{2a}$ is optionally substituted with 1-4 halogen or $C_1$-$C_6$ alkoxy groups;

each $Z^3$ is independently oxo, halogen, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$; wherein any alkenyl, alkynyl, carbocyclyl, aryl, heteroaryl or heterocyclyl portions of $Z^3$ is optionally substituted with 1-4 halogen; and each $Z^4$ is independently oxo, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$, wherein any alkenyl, alkynyl, carbocyclyl, aryl, heteroaryl or heterocyclyl portions of $Z^4$ is optionally substituted with 1-4 halogen.

In one embodiment, the compound of Formula IV is:

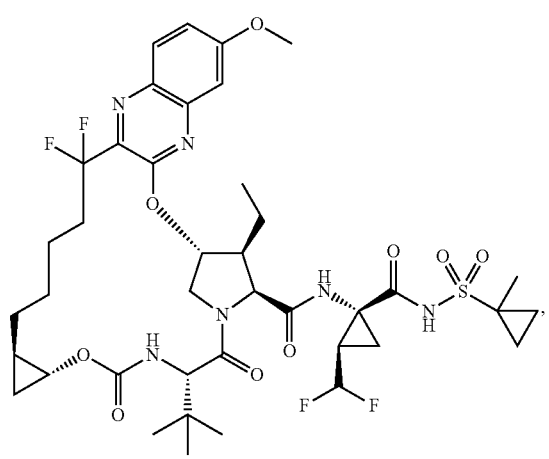 [SMILES: CC[C@@H]1[C@@H]2CN(C(=O)[C@H](C(C)(C)C)NC(=O)O[C@@H]3C[C@H]3CCCCC(F)(F)c3nc4ccc(OC)cc4nc3O2)[C@@H]1C(=O)N[C@]1(C(=O)NS(=O)(=O)C2(C)CC2)C[C@H]1C(F)F]

or a pharmaceutically acceptable salt thereof. This compound is also known as voxilaprevir.

D. Example Anti-HBV Agents

An anti-HBV agent may be a compound that inhibits HBV infection, gene expression, DNA production, or DNA replication. In one embodiment, the anti-HBV agent is a HBV reverse transcriptase inhibitor. In one embodiment, the anti-HBV agent is a nucleoside analogue. Non-limiting examples of anti-HBV agent include tenofovir alafenamide, tenofovir, lamivudine, adefovir, telbivudine and entecavir.

Tenofovir, or tenofovir disoproxil, is a nucleotide analog reverse-transcriptase inhibitor (NtRTI). Tenofovir selectively inhibits viral reverse transcriptase. Once incorporated into a growing DNA strand, tenofovir causes premature termination of DNA transcription, preventing viral replication. Tenofovir has a chemical name of bis{[(isopropoxycarbonyl)oxy]methyl} ({[(2R)-1-(6-amino-9H-purin-9-yl)-2-propanyl]oxy}methyl)phosphonate, and the structure of:

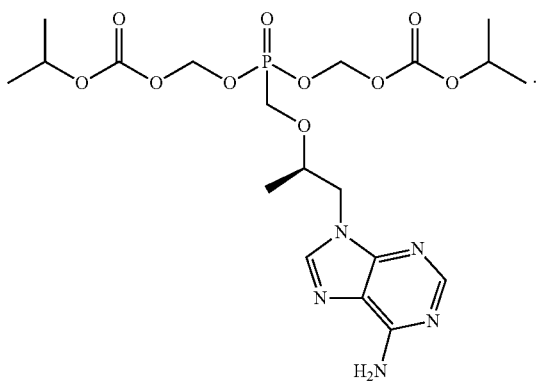 [SMILES: CC(C)OC(=O)OCOP(=O)(CO[C@H](C)Cn1cnc2c(N)ncnc21)OCOC(=O)OC(C)C]

Tenofovir is commercially available under the tradename Viread™. The recommended dose, in adults and pediatric patients ≥12 years of age (≥35 kg), is one 300 mg tablet, once daily, taken orally, without regard to food.

Tenofovir alafenamide is a nucleotide reverse transcriptase inhibitor and a prodrug of tenofovir. Tenofovir alafenamide has a chemical name of isopropyl (2S)-2-[[[(1R)-2-(6-aminopurin-9-yl)-1-methyl-ethoxy]methyl-phenoxy-phosphoryl]amino]propanoate, and the structure of:

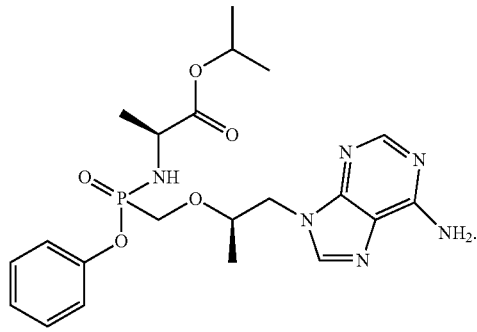 [SMILES: CC(C)OC(=O)[C@H](C)NP(=O)(CO[C@H](C)Cn1cnc2c(N)ncnc21)Oc1ccccc1]

Tenofovir alafenamide is commercially available under the tradename Vemlidy™. The recommended dose in adults is one 25 mg tablet once daily, taken orally with food.

Lamivudine is an analogue of cytidine. It can inhibit the reverse transcriptase of hepatitis B virus. It is phosphorylated to active metabolites that compete for incorporation into viral DNA. The lack of a 3'—OH group in the incorporated nucleoside analogue prevents the formation of the 5' to 3' phosphodiester linkage essential for DNA chain elongation, and therefore, the viral DNA growth is terminated. Lamivudine has the chemical name of 4-Amino-1-[(2R,5S)-2-(hydroxymethyl)-1,3-oxathiolan-5-yl]-1,2-dihydropyrimidin-2-one and the structure of:

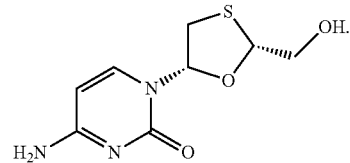 [SMILES: Nc1ccn([C@@H]2CS[C@H](CO)O2)c(=O)n1]

Lamivudine is commercially available under the tradename Epivir™. The recommended dose in HBV patients is one 100 mg tablet once daily.

Adefovir is a reverse transcriptase inhibitor. It has a chemical name of {[2-(6-amino-9H-purin-9-yl)ethoxy]methyl}phosphonic acid and the structure of:

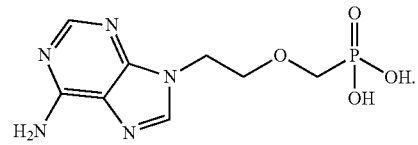

Adefovir is commercially available under the tradename Hepsera™. The recommended dose is 10 mg orally once daily, without regard to food.

Telbivudine is a synthetic thymidine β-L-nucleoside analogue. It is the L-isomer of thymidine. Telbivudine impairs hepatitis B virus (HBV) DNA replication by leading to chain termination. It differs from the natural nucleotide only with respect to the location of the sugar and base moieties, taking on a levorotatory configuration versus a dextrorotatory configuration as do the natural deoxynucleosides. Telbivudine has a chemical name of 1-[(2S,4R,5S)-4-hydroxy-5-hydroxymethyltetrahydorfuran-2-yl]-5-methyl-1-H-pyrimidine-2,4-dione and the structure of:

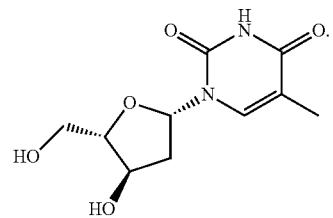 [SMILES: Cc1cn([C@@H]2C[C@@H](O)[C@H](CO)O2)c(=O)[nH]c1=O]

The recommended dose of telbivudine 600 mg once daily with or without food.

Entecavir is a nucleoside analog, and more specifically a deoxyguanosine analogue that inhibits reverse transcription, DNA replication and transcription in the viral replication process. Entecavir reduces the amount of HBV in the blood by reducing its ability to multiply and infect new cells. Entecavir has a chemical name of 2-Amino-9-[(1S,3R,4S)-4-hydroxy-3-(hydroxymethyl)-2-methylidenecyclopentyl]-1H-purin-6-one and the structure of:

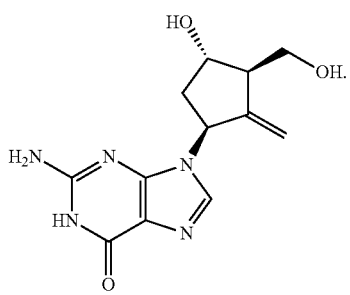 [SMILES: C=C1[C@H](CO)[C@@H](O)C[C@@H]1n1cnc2c(=O)[nH]c(N)nc21]

Entecavir is commercially available under the trade name Baraclude™. The recommended dose for entecavir in adults with chronic HVB infection is 0.5 mg or 1 mg daily.

E. Alternative Compounds

It is to be noted that all isomers (including stereoisomers, enantiomers, and diastereomers) and racemic mixtures, tautomers, isotopes, salts, pharmaceutically acceptable salts, polymorphs, pseudopolymorphs, prodrugs and metabolites are embraced by the present disclosure.

The term "stereoisomer" as used herein refers to the stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

"Isomers" are different compounds that have the same molecular formula. Isomers include stereoisomers, enantiomers and diastereomers.

"Diastereomers" are stereoisomers that have at least two asymmetric atoms, but which are not mirror-images of each other.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

The term "stereoisomers" refers to compounds which have identical chemical constitution, but differ with regard to the arrangement of the atoms or groups in space.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. In other words, the chiral centers apparent from the depictions are provided as the chiral isomers or racemic mixtures.

Both racemic and diastereomeric mixtures, as well as the individual optical isomers isolated or synthesized, substantially free of their enantiomeric or diastereomeric partners, are all within the scope of the disclosure. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted.

Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

The compounds disclosed herein can also exist as tautomeric isomers in certain cases. Although only one delocalized resonance structure may be depicted, all such forms are contemplated within the scope of the disclosure. For example, ene-amine tautomers can exist for purine, pyrimidine, imidazole, guanidine, amidine, and tetrazole systems and all their possible tautomeric forms are within the scope of the disclosure.

It is understood by one skilled in the art that this disclosure also includes any compound claimed that may be enriched at any or all atoms above naturally occurring isotopic ratios with one or more isotopes such as, but not limited to, deuterium ($^2$H or D). As a non-limiting example, a —$CH_3$ group may be replaced by —$CD_3$.

Specific values listed below for radicals, substituents, and ranges are for illustration only; they do not exclude other defined values or other values within defined ranges for the radicals and substituents.

Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein each X is independently selected from H or a $C_1$-$C_4$ alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of the compounds described herein or a stereoisomer, or a mixture of stereoisomers, or another compound disclosed herein. All salts, whether or not derived from a physiologically acceptable acid or base, are within the scope of the present disclosure.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines.

Finally, it is to be understood that the compositions herein comprise compounds disclosed herein in their un-ionized, as well as zwitterionic form, and combinations with stoichiometric amounts of water as in hydrates.

The compounds described herein and their pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant disclosure may exist due to differences in crystal packing (packing pseudopolymorphism) or due to differences in packing between different conformers of the same molecule (conformational pseudopolymorphism). The instant disclosure comprises all polymorphs and pseudopolymorphs of the compounds described herein and their pharmaceutically acceptable salts.

The compounds described herein and their pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant disclosure. The instant disclosure comprises all amorphous forms of the compounds described herein and their pharmaceutically acceptable salts.

For therapeutic use, salts of active ingredients of the compounds of the disclosure will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present disclosure.

Finally, it is to be understood that the compositions herein comprise compounds of the disclosure in their un-ionized, as well as zwitterionic form, and combinations with stoichiometric amounts of water as in hydrates.

The compounds described herein may have chiral centers, e.g. chiral carbon or phosphorus atoms. The compounds of the disclosure thus include racemic mixtures of all stereoisomers, including enantiomers, diastereomers, and atropisomers. In addition, the compounds of the disclosure include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the disclosure. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

"Prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

Also falling within the scope of this disclosure are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the disclosure includes novel and unobvious compounds produced by a process comprising contacting a compound of this disclosure with a mammal for a period of time sufficient to yield a metabolic product thereof. Such products typically are identified by preparing a radiolabelled (e.g. $^{14}C$ or $^3H$) compound of the disclosure, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the disclosure even if they possess no anti hepatitis B virus activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the disclosure typically will be stable in the digestive system but may be substantially hydrolyzed to the parental drug in the digestive lumen, liver or other metabolic organ, or within cells in general.

For both the inhibitors, whenever a compound described herein is substituted with more than one of the same designated group, e.g., "R" or "R¹", then it will be understood that the groups may be the same or different, i.e., each group is independently selected. Wavy lines, ⁓⁓⁓⁓, indicate the site of covalent bond attachments to the adjoining substructures, groups, moieties, or atoms.

Selected substituents comprising the compounds described herein are present to a recursive degree. In this context, "recursive substituent" means that a substituent may recite another instance of itself. Because of the recursive nature of such substituents, theoretically, a large number of compounds may be present in any given embodiment. For example, $R^x$ comprises a $R^y$ substituent. $R^y$ can be R. R can be $Z^3$. $Z^3$ can be $Z^4$ and $Z^4$ can be R or comprise substituents comprising $R^y$. Alternatively, $Z^3$ can be $Z^5$ which can comprise substituents comprising Ry. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $Z^3$ and $R^y$ are recursive substituents in certain embodiments. Typically, each recursive substituent can independently occur 20, 19, 18, 17, 16, 15, 14, 13, 12, 11, 10, 9, 8, 7, 6, 5, 4, 3, 2, 1, or 0, times in a given embodiment. More typically, each recursive substituent can independently occur 12 or fewer times in a given embodiment. Even more typically, each recursive substituent can independently occur 3 or fewer times in a given embodiment. For example, $Z^3$ will occur 0 to 8 times, $R^y$ will occur 0 to 6 times in a given embodiment. Even more typically, $Z^3$ will occur 0 to 6 times and $R^y$ will occur 0 to 4 times in a given embodiment.

Recursive substituents are an intended aspect of the disclosure. One of ordinary skill in the art of medicinal chemistry understands the versatility of such substituents. To the degree that recursive substituents are present in an embodiment of the disclosure, the total number will be determined as set forth above.

The compounds of the present disclosure can be prepared by methods known to one of skill in the art or based on the examples in the publications cited herein.

III. DEFINITIONS

Unless stated otherwise, the following terms and phrases as used herein are intended to have the following meanings:

When a cyclic group (e.g. cycloalkyl, carbocyclyl, bicyclic carbocyclyl, heteroaryl, heterocyclyl) is limited by a number or range of numbers, the number or numbers refer to the number of atoms making up the cyclic group, including any heteroatoms. Therefore, for example, a 4-8 membered heterocyclyl group has 4, 5, 6, 7 or 8 ring atoms.

"Alkenyl" refers to a straight or branched chain hydrocarbyl with at least one site of unsaturation, e.g., a ($sp^2$) carbon-($sp^2$)carbon double bond. For example, an alkenyl group can have 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=CH$_2$) and allyl (—CH$_2$CH=CH$_2$).

"Alkenylene" refers to an alkene having two monovalent radical centers derived by the removal of two hydrogen atoms from the same or two different carbon atoms of a parent alkene. Exemplary alkenylene radicals include, but are not limited to, 1,2-ethenylene (—CH=CH—) or prop-1-enylene (—CH$_2$CH=CH—).

"Alkoxy" is RO— where R is alkyl, as defined herein. Non-limiting examples of alkoxy groups include methoxy, ethoxy and propoxy.

"Alkyl" refers to a saturated, straight or branched chain hydrocarbyl radical. For example, an alkyl group can have 1 to 8 carbon atoms (i.e., ($C_1$-$C_8$) alkyl) or 1 to 6 carbon atoms (i.e., ($C_1$-$C_6$ alkyl) or 1 to 4 carbon atoms. Examples of alkyl groups include, but are not limited to, methyl, ethyl, propyl, isopropyl, butyl, isobutyl, t-butyl, pentyl, hexyl, heptyl, octyl, nonyl and decyl.

"Alkylene" refers to an alkyl having two monovalent radical centers derived by the removal of two hydrogen atoms from the same or two different carbon atoms of a parent alkane. Examples of alkylene radicals include, but are not limited to, methylene (—CH$_2$—), ethylene (—CH$_2$CH$_2$—), propylene (—CH$_2$CH$_2$CH$_2$—) and butylene (—CH$_2$CH$_2$CH$_2$CH$_2$—).

"Alkynyl" refers to a straight or branched chain hydrocarbon with at least one site of unsaturation, e.g., a (sp) carbon-(sp)carbon triple bond. For example, an alkynyl group can have 2 to 8 carbon atoms ($C_2$-$C_8$ alkyne) or 2 to 6 carbon atoms ($C_2$-$C_6$ alkynyl). Examples of alkynyl groups include, but are not limited to, acetylenyl (—C≡CH) and propargyl (—CH$_2$C≡CH) groups.

"Alkynylene" refers to an alkynyl having two monovalent radical centers derived by the removal of two hydrogen atoms from the same or two different carbon atoms of a parent alkyne. Typical alkynylene radicals include, but are not limited to, acetylene (—C≡C—), propargylene (—CH$_2$C≡C—), and 1-pentynylene (—CH$_2$CH$_2$CH$_2$C≡C—).

"Aryl" refers to a single all carbon aromatic ring or a multiple condensed all carbon ring system (e.g., a fused multicyclic ring system) wherein at least one of the rings is aromatic. For example, an aryl group can have 6 to 20 carbon atoms, 6 to 14 carbon atoms, or 6 to 12 carbon atoms. It is to be understood that the point of attachment of a multiple condensed ring system, as defined above, can be at any position of the ring system including an aromatic or a carbocyclyl portion of the ring. Examples of aryl groups include, but are not limited to, phenyl, naphthyl, tetrahydronaphthyl and indanyl.

"Arylene" refers to an aryl as defined herein having two monovalent radical centers derived by the removal of two hydrogen atoms from two different carbon atoms of a parent aryl. Typical arylene radicals include, but are not limited to, phenylene, e.g.,

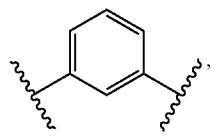 [SMILES: *c1cccc(*)c1]

and naphthylene, e.g.,

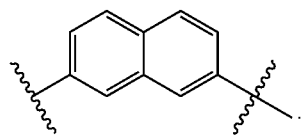

"Bicyclic carbocyclyl" refers to a 5-14 membered saturated or partially unsaturated bicyclic fused, bridged, or spiro ring hydrocarbon attached via a ring carbon. In a spiro bicyclic carbocyclyl, the two rings share a single common carbon atom. In a fused bicyclic carbocyclyl, the two rings share two common and adjacent carbon atoms. In a bridged bicyclic carbocyclyl, the two rings share three or more common, non-adjacent carbon atoms. Examples of bicyclic carbocyclyl groups include, but are not limited to spiro bicyclic carbocyclyl groups wherein two carbocyclyl rings share one common atom

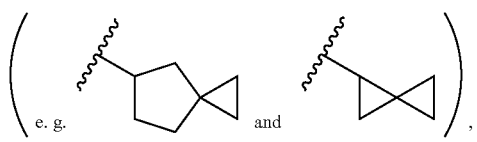

fused bicyclic carbocyclyl groups wherein two carbocyclyl rings share two common atoms

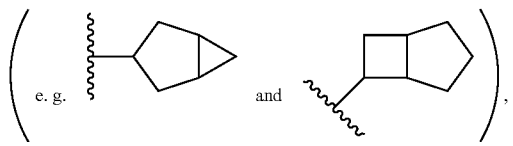

and bridged bicyclic carbocyclyl groups wherein two carbocyclyl rings share three or more (such as 3, 4, 5 or 6) common atoms

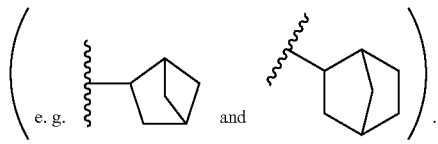

"Bicyclic carbocyclylene" refers to a bicyclic carbocyclyl, as defined above, having two monovalent radical centers derived from the removal of two hydrogen atoms from the same or two different carbon atom of a parent bicyclic carbocyclyl. Examples of bicyclic carbocyclylene groups include, but are not limited to, spiro bicyclic carbocyclylene groups wherein two carbocyclyl rings share one common atom

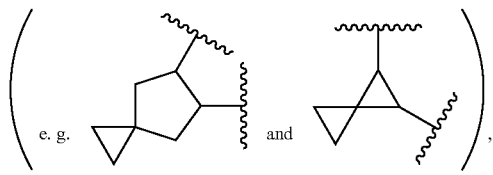

fused bicyclic carbocyclylene groups wherein two carbocyclyl rings share two common atoms

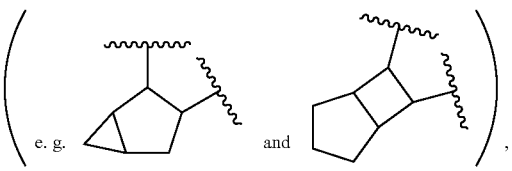

and bridged bicyclic carbocyclylene groups wherein two carbocyclyl rings share three or more (such as 3, 4, 5 or 6) common atoms

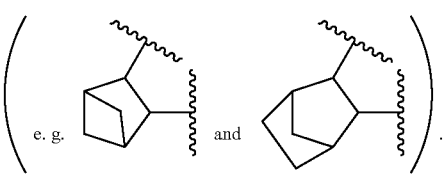

"Carbocyclyloxy" is RO— where R is carbocyclyl, as defined herein.

"Bicyclic carbocyclyloxy" is RO— where R is bicyclic carbocyclyl, as defined herein.

"Carbocyclyl", and "carbocycle" refers to a hydrocarbyl group containing one saturated or partially unsaturated ring structure, attached via a ring carbon. In various embodiments, carbocyclyl refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Carbocyclylene" (as well as "carbocyclene") refers to a carbocyclyl, as defined herein, having two monovalent radical centers derived by the removal of two hydrogen atoms from the same or two different carbon atoms of a parent carbocyclyl. Examples of carbocyclene include, but are not limited to, cyclopropylene, cyclobutylene, cyclopentylene and cyclohexylene.

"Carbocyclylalkyl" refers to a hydrocarbyl group containing one saturated or partially unsaturated ring structure attached to an alkyl group, attached via a ring carbon or an alkyl carbon. In various embodiments, carbocyclylalkyl refers to a saturated or a partially unsaturated $C_1$-$C_{12}$ carbocyclylalkyl moiety, examples of which include cyclopropylalkyl, cyclobutylalkyl, cyclopropylethyl, and cyclopropylpropyl.

"Carbocyclylalkylene" refers to a carbocyclylalkyl, as defined herein, having two monovalent radical centers derived by the removal of two hydrogen atoms from the same or two different carbon atoms of a parent cycloalkylalkyl. Examples of cycloalkylene include, but are not limited to, cyclopropylmethylene and cyclopropylmethylene.

"Cycloalkyl" refers to a hydrocarbyl group containing one saturated ring structure, attached via a ring carbon. In various embodiments, cycloalkyl refers to a saturated $C_3$-$C_{12}$ cyclic moiety, examples of which include cyclopropyl, cyclobutyl, cyclopentyl, cyclohexyl, cycloheptyl and cyclooctyl.

"Cycloalkoxy" is RO— where R is cycloalkyl, as defined herein.

"Direct bond" refers a covalent bond between two atoms.

"Halo" or "halogen" refers to chloro (—Cl), bromo (—Br), fluoro (—F) or iodo (—I).

"Haloalkenyl" refers to alkenyl group, as defined herein, substituted with one or more halogen atoms.

"Haloalkoxy" refers to alkoxy, as defined herein, substituted with one or more halogen atoms.

"Haloalkyl" refers to an alkyl group, in which one or more hydrogen atoms of the alkyl group is replaced with a halogen atom. Examples of haloalkyl groups include, but are not limited to, —CF$_3$, —CHF$_2$, —CFH$_2$ and —CH$_2$CF$_3$.

"Haloalkylene" refers to alkylene group, as defined herein, substituted with one or more halogen atoms.

"Heteroalkyl" refers to an alkyl group, as defined herein, in which one or more carbon atoms is replaced with an oxygen, sulfur, or nitrogen atom.

"Heteroalkylene" refers to an alkylene group, as defined herein, in which one or more carbon atoms is replaced with an oxygen, sulfur, or nitrogen atom.

"Heteroalkenyl" refers to an alkenyl group, as defined herein, in which one or more carbon atoms is replaced with an oxygen, sulfur, or nitrogen atom.

"Heteroalkenylene" refers to heteroalkenyl group, as defined above, having two monovalent radical centers derived by the removal of two hydrogen atoms from the same or two different atoms of a parent heteroalkenyl group.

"Heteroaryl" refers to a single aromatic ring that has at least one atom other than carbon in the ring, wherein the atom is selected from the group consisting of oxygen, nitrogen and sulfur; the term also includes multiple condensed ring systems that have at least one such aromatic ring. For example, heteroaryl includes monocyclic, bicyclic or tricyclic ring having up to 6 atoms in each ring, wherein at least one ring is aromatic and contains from 1 to 4 heteroatoms in the ring selected from the group consisting of oxygen, nitrogen and sulfur. The rings of the multiple condensed ring system can be connected to each other via fused, spiro and bridged bonds when allowed by valency requirements. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazolyl, pyrrolyl, pyridazinyl, pyrazinyl, quinolinyl, isoquinolinyl, quinoxalinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylene" refers to a heteroaryl, as defined above, having two monovalent radical centers derived by the removal of two hydrogen atoms from the same or two different carbon atoms or the removal of a hydrogen from one carbon atom and the removal of a hydrogen atom from one nitrogen atom of a parent heteroaryl group. Non-limiting examples of heteroarylene groups are:

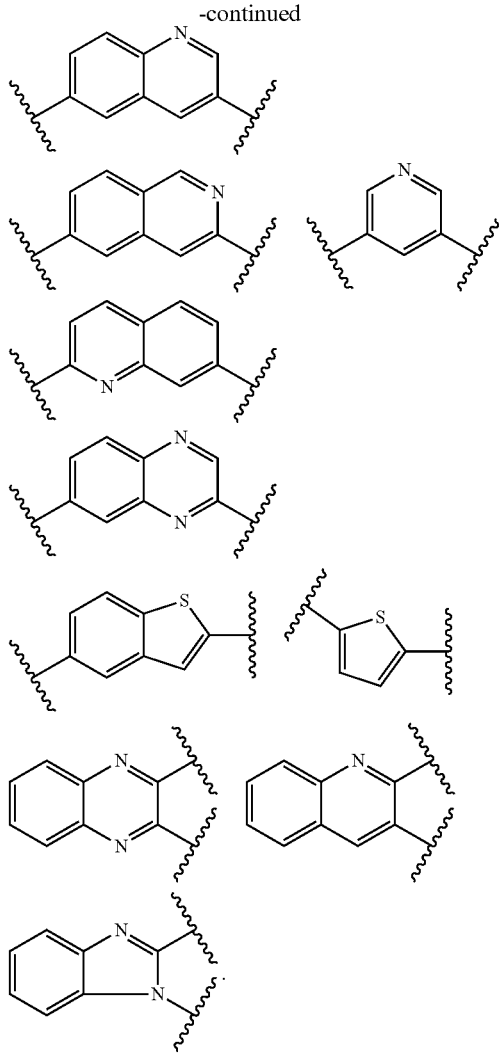

"Heterocyclyl" refers to a saturated or partially unsaturated monocyclic, bicyclic or tricyclic group of 2 to 14 ring-carbon atoms and, in addition to ring-carbon atoms, 1 to 4 heteroatoms selected from nitrogen, oxygen and sulfur. Bi- or tricyclic heterocyclyl groups may have fused, bridged, or spiro ring connectivity. In various embodiments the heterocyclic group is attached to another moiety through carbon or through a heteroatom. Examples of heterocyclyl include without limitation azetidinyl, oxazolinyl, isoxazolinyl, oxetanyl, tetrahydropyranyl, tetrahydrothiopyranyl, tetrahydroisoquinolinyl, 1,4-dioxanyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, chromanyl, dihydropyranoquinoxalinyl, tetrahydroquinoxalinyl, tetrahydroquinolinyl, dihydropyranoquinolinyl and tetrahydrothienyl and N-oxides thereof. A spiro bicyclic heterocyclyl group refers to a bicyclic heterocyclyl group wherein the two rings of the bicyclic heterocyclyl group share one common atom. A fused bicyclic heterocyclyl group refers to a bicyclic heterocyclyl group wherein the two rings of the bicyclic heterocyclyl group share two common atoms. A bridged bicyclic heterocyclyl group refers to a bicyclic heterocyclyl group wherein the two rings of the bicyclic heterocyclyl group share three or more (such as 3, 4, 5 or 6) common atoms.

"Heterocyclene" refers to a heterocyclyl, as defined herein, having two monovalent radical centers derived from the removal of two hydrogen atoms from the same or two different carbon atoms, through a carbon and a heteroatom, or through two heteroatoms of a parent heterocycle.

The term "optionally substituted" refers to a moiety wherein all substituents are hydrogen or wherein one or more of the hydrogens of the moiety are replaced by non-hydrogen substituents; that is to say the moiety that is optionally substituted is either substituted or unsubstituted.

IV. PHARMACEUTICAL COMPOSITIONS

In certain embodiments, the compounds are administered in pharmaceutical compositions. The compounds of this disclosure may be formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. In some embodiments, the pH of the formulations ranges from about 2 to about 5, but is ordinarily about 3 to 4.

While it is possible for the active ingredients to be administered alone it may be preferable to present them as pharmaceutical compositions. The formulations, both for veterinary and for human use, of the disclosure comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the disclosure include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical compositions according to the present disclosure comprise a combination according to the disclosure together with one or more pharmaceutically acceptable carriers or excipients and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the disclosure contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin and Captisol (=Sulfobutyl ether beta-cyclodextrin; SEB-beta-CD).

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of hepatitis B virus infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this disclosure may include other agents conventional in the art having regard to the type of formulation in question, for example those suitable for oral administration may include flavoring agents.

The disclosure further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the disclosure are used to provide controlled release pharmaceutical compositions containing as active ingredient one or more compounds of the disclosure ("controlled release formulations") in which the release of the active ingredient are controlled and regulated to allow less frequency dosing or to improve the pharmacokinetic or toxicity profile of a given active ingredient.

The inhibitors may be administered as a co-formulation. Methods of co-formulation are known in the art. For example, the co-formulation of ledipasvir and sofosbuvir is thoroughly described in WO 2014/12098. In one embodiment, the pharmaceutical composition comprises:
  a) an effective amount of ledipasvir wherein the ledipasvir is substantially amorphous; and
  b) an effective amount of sofosbuvir wherein the sofosbuvir is substantially crystalline, and further wherein the composition exhibits unexpected properties.

In one embodiment, ledipasvir is formulated as a solid dispersion comprising ledipasvir dispersed within a polymer matrix formed by a pharmaceutically acceptable polymer. In one embodiment, the polymer is copovidone. In one embodiment, wherein the weight ratio of ledipasvir to copovidone in the solid dispersion is about 1:1.

In one embodiment, the pharmaceutical composition comprises:
  a) about 40% w/w of sofosbuvir and
  b) about 18% w/w of the solid dispersion comprising ledipasvir.

In one embodiment, the pharmaceutical composition further comprises:
  a) about 5 to about 25% w/w lactose monohydrate,
  b) about 5 to about 25% w/w microcrystalline cellulose,
  c) about 1 to about 10% w/w croscarmellose sodium,
  d) about 0.5 to about 3% w/w colloidal silicon dioxide, and
  e) about 0.1 to about 3% w/w magnesium stearate.

Also useful in the methods described herein is a pharmaceutical dosage form comprising the pharmaceutical composition described herein comprising about 90 mg of ledipasvir and about 400 mg of sofosbuvir. In one embodiment, the pharmaceutical dosage comprises ledipasvir formulated as a solid dispersion within a polymer matrix of copovidone. In one embodiment, the amount of copovidone is about 90 mg. In one embodiment, the pharmaceutical dosage form further comprises:
  (a) about 165 mg of lactose monohydrate;
  (b) about 180 mg of microcrystalline cellulose;
  (c) about 50 mg of croscarmellose sodium;
  (d) about 10 mg of colloidal silicon dioxide; and
  (e) about 15 mg of magnesium stearate.

In one embodiment, the compsoition, co-formulation, or pharmaceutical dosage form further comprises another anti-HBV agent. In one embodiment, the anti-HBV agent is selected from tenofovir alafenamide, tenofovir, lamivudine, adefovir, telbivudine or entecavir. In one embodiment, the anti-HBV agent is tenofovir alafenamide. In one embodiment, the tenofovir alafenamide is present at an amount of 25 mg. In one embodiment, the tenofovir alafenamide is present at an amount less than 25 mg, such as 20 mg or 15 mg. In one embodiment, the pharmaceutical dosage form is in the form of a tablet comprising a film coating.

V. ROUTES OF ADMINISTRATION

One or more compounds of the disclosure (herein referred to as the active ingredients) are administered by any route appropriate to the condition to be treated. Suitable routes include oral, rectal, nasal, pulmonary, topical (including buccal and sublingual), vaginal and parenteral (including subcutaneous, intramuscular, intravenous, intradermal, intrathecal and epidural), and the like. In certain embodiments, the compounds disclosed herein are administered by intravenous injection. It will be appreciated that the preferred route may vary with for example the condition of the recipient. An advantage of the compounds of this disclosure is that they are orally bioavailable and can be dosed orally.

Effective dose of active ingredient depends at least on the nature of the condition being treated, toxicity, whether the compound is being used prophylactically (lower doses) or against an active viral infection, the method of delivery, and the pharmaceutical composition, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

In the methods of the present disclosure for the treatment of a hepatitis B virus infection, the compounds of the present disclosure can be administered at any time to a human who may come into contact with humans suffering from a hepatitis B virus infection or is already suffering from a hepatitis B virus infection. In some embodiments, the compounds of the present disclosure can be administered prophylactically to humans coming into contact with humans suffering from a hepatitis B virus infection. In some embodiments, administration of the compounds of the present disclosure can be to humans testing positive for a hepatitis B virus infection but not yet showing symptoms of a hepatitis B virus infection. In some embodiments, administration of the compounds of the present disclosure can be to humans upon commencement of symptoms of a hepatitis B virus infection.

Effective dose of active ingredient depends at least on the nature of the condition being treated, toxicity, whether the compound is being used prophylactically (lower doses) or against an active viral infection, the method of delivery, and the pharmaceutical composition, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

The effective dose of a compound of the present disclosure for treating the hepatitis B virus infection can depend on whether the dose is to be used prophylactically or to treat a human already suffering from a hepatitis B virus infection. Moreover, the dose can depend on whether the human suffering from a hepatitis B virus infection does not yet show symptoms or is already showing symptoms of a hepatitis B virus infection. Larger doses may be necessary for treating humans testing positive for a hepatitis B virus infection and for humans showing symptoms of a hepatitis B virus infection as compared to humans receiving prophylactic treatment.

Any suitable period of time for administration of the compounds of the present disclosure is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 2, 3, 4, 5, 6, 7, 8, 9, 10, 11, 12, 13, or 14 weeks. Longer periods of administration are also contemplated. The time for administration can depend on whether the compound is being administered prophylactically or to treat a human suffering from an a hepatitis B virus infection. For example, a prophylactic administration can be for a period of time while the human is in regular contact with other humans suffering from an a hepatitis B virus infection, and for a suitable period of time following the last contact with a human suffering from an a hepatitis B virus infection. For humans already suffering from an a hepatitis B virus infection, the period of administration can be for any length of time necessary to treat the patient and a suitable period of time following a negative test for a hepatitis B virus infection to ensure the a hepatitis B virus infection does not return.

In various methods, ledipasvir or another NS5A inhibitor is administered in an amount ranging from about 10 mg/day to about 200 mg/day. For example, the amount of the compound can be about 30 mg/day, about 45 mg/day, about 60 mg/day, about 90 mg/day, about 120 mg/day, about 135 mg/day, about 150 mg/day, or about 180 mg/day. In some methods, ledipasvir is administered at about 90 mg/day. In various methods, the NS5A inhibitor is administered in an amount ranging from about 50 mg/day to about 800 mg/day. For example, the amount of the inhibitor can be about 100 mg/day, about 200 mg/day, or about 400 mg/day.

In various methods, sofosbuvir or another NS5B inhibitor is administered in an amount ranging from about 10 mg/day to about 1000 mg/day. For example, the amount of sofosbuvir can be about 100 mg/day, about 200 mg/day, about 300 mg/day, about 400 mg/day, about 500 mg/day, about 600 mg/day, about 700 mg/day, about 800 mg/day. In some methods, sofosbuvir is administered at about 400 mg/day.

In various methods, the anti-HBV agent is administered in an amount ranging from about 10 mg/day to about 1000 mg/day. For example, the amount of tenofovir alafenamide can be about 5 mg/day, about 10 mg/day, about 15 mg/day, about 20 mg/day, about 25 mg/day.

VI. COMBINATION THERAPY

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HBV Combination Therapy

In certain embodiments, when a compound disclosed herein is combined with one or more additional therapeutic agents as described above, the components of the composition are administered as a simultaneous or sequential regimen. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a patient, for example as a solid dosage form for oral administration.

In certain embodiments a compound of Formula (I) is formulated as a tablet, which may optionally contain one or more other compounds useful for treating HBV. In certain embodiments, the tablet can contain another active ingredient for treating HBV.

In certain embodiments, such tablets are suitable for once daily dosing.

HBV Combination Therapy

In the above embodiments, the additional therapeutic agent may be an anti-HBV agent. For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In certain embodiments, a compound of Formula (I) is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, CCC-0975, elvucitabine, ezetimibe, cyclosporin A, gentiopicrin (gentiopicroside), JNJ-56136379, nitazoxanide, birinapant, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US 2015/0210210682 (Roche), US 2016/0122344 (Roche), WO2015173164, and WO2016023877.

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B recombinant hepatitis B vaccine (intramuscular, Kangtai Biological Products), recombinant hepatitis B vaccine (*Hansenual polymorpha* yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, INO-9112, polymer polyethyleneimine (PEI), Gepon, VGV-1, MOR-22, BMS-936559, RO-7011785, RO-6871765, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, TMX-30X, TMX-202, RG-7863, RG-7795, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON@, interferon alfa-n1 (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Biprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-Lymphocyte-Associated Protein 4 (Ipi4) Inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404.

Short Interfering RNAs (siRNA) and ddRNAi.

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucleotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Example of farnesoid x receptor agonist such as EYP-001.

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies such as HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience)

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include AT-130, GLS4, NVR-1221, NVR-3778, BAY 41-4109, morphothiadine mesilate, JNJ-379, and DVR-23. Capsid assembly inhibitors such as AB-423.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), and WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche).

Retinoic Acid-inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301, TAK-117, HMPL-689, tenalisib, voxtalisib, and CLR-1401.

Indoleamine-2, 3-Dioxygenase (IDO) Pathway Inhibitors

Examples of IDO inhibitors include epacadostat (INCB24360), resminostat (4SC-201), indoximod, F-001287, SN-35837, NLG-919, GDC-0919, GBV-1028, GBV-1012, NKTR-218, and the compounds disclosed in US20100015178 (Incyte).

PD-1 Inhibitors

Examples of PD-1 inhibitors include nivolumab, pembrolizumab, pidilizumab, BGB-108, SHR-1210, PDR-001, PF-06801591, IBI-308, GB-226, STI-1110, and mDX-400.

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, and BMS-936559.

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US2014/0275092 (Genentech/Constellation Pharmaceuticals), US20140371195 (Epitherapeutics) and US20140371214 (Epitherapeutics), US2016/0102096 (Epitherapeutics), US2014/0194469 (Quanticel), US2014/0171432, US2014/0213591 (Quanticel), US2016/0039808 (Quanticel), WO2014151945 (Quanticel), WO2014164708 (Quanticel).

Examples of KDM1 inhibitors include the compounds disclosed in U.S. Pat. No. 9,186,337B2 (Oryzon Genomics), and GSK-2879552, RG-6016, ORY-2001.

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

HBV Combination Therapy

In one embodiment, pharmaceutical compositions comprising a compound disclosed herein, or a pharmaceutically acceptable salt thereof, in combination with one or more (e.g., one, two, three, four, one or two, or one to three, or one to four) additional therapeutic agents and a pharmaceutically acceptable carrier, diluent, or excipient are provided.

HBV DNA Polymerase Inhibitor Combination Therapy

In a specific embodiment, a compound disclosed herein, or a pharmaceutically acceptable salt thereof, is combined with an HBV DNA polymerase inhibitor. In another specific embodiment, a compound disclosed herein, or a pharmaceutically acceptable salt thereof, is combined with an HBV DNA polymerase inhibitor and at least one additional therapeutic agent selected from the group consisting of: immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, cytotoxic T-lymphocyte-associated protein 4 (ipi4) inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, epigenetic modifiers, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, IDO inhibitors, and hepatitis B virus replication inhibitors.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

HBV Drug Combination Therapy

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, interferon alpha receptor ligands, hyaluronidase inhibitors, recombinant IL-7, HBsAg inhibitors, HBsAg secretion or assembly inhibitors, compounds targeting HBcAg, cyclophilin inhibitors, HBV vaccines, HBV viral entry inhibitors, NTCP inhibitors, antisense oligonucleotide targeting viral mRNA, siRNA, miRNA gene therapy agents, endonuclease modulators, inhibitors of ribonucleotide reductase, hepatitis B virus E antigen inhibitors, recombinant SRA proteins, src kinase inhibitors, HBx inhibitors, cccDNA inhibitors, sshRNAs, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, and TCR-like antibodies), CCR2 chemokine antagonists, thymosin agonists, cytokines, nucleoprotein modulators (HBV core or capsid protein modulators), stimulators of retinoic acid-inducible gene 1, stimulators of RIG-I like receptors, stimulators of NOD2, stimulators of NOD1, IDO inhibitors, recombinant thymosin alpha-1, Arginase inhibitors, STING agonists, PI3K inhibitors, lymphotoxin beta receptor activators, natural killer cell receptor 2B4 inhibitors, Lymphocyte-activation gene 3 inhibitors, CD160 inhibitors, ipi4 inhibitors, CD137 inhibitors, killer cell lectin-like receptor subfamily G member 1 inhibitors, TIM-3 inhibitors, B- and T-lymphocyte attenuator inhibitors, epigenetic modifiers, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Ax1, modulators of Mer, modulators of Tyro, gene modifiers or editors such as CRISPR (including CRISPR Cas9), zinc finger nucleases or synthetic nucleases (TALENs), IAPs inhibitors, SMAC mimetics, KDM5 inhibitors, and hepatitis B virus replication inhibitors.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®) or lamivudine (EPIVIR-HBV®) and at least a second additional therapeutic agent selected from the group consisting of peginterferon alfa-2b (PEG-INTRON®), MULTIFERON®, interferon alpha 1b (HAPGEN®), interferon alpha-2b (INTRON A®), pegylated interferon alpha-2a (PEGASYS®), interferon alfa-n1 (HUMOFERON®), ribavirin, interferon beta-1a (AVONEX®), Bioferon, Ingaron, Inmutag (Inferon), Algeron, Roferon-A, Oligotide, Zutectra, Shaferon, interferon alfa-2b (AXXO), Alfaferone, interferon alfa-2b (Bio-Generic Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon- B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon, and celmoleukin.

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, Arginase inhibitors, PI3K inhibitors, PD-1 inhibitors, PD-L1 inhibitors, IDO inhibitors and stimulators of NOD2.

In a particular embodiment, a compound disclosed herein, or a pharmaceutically acceptable salt thereof, is combined with a first additional therapeutic agent selected from the group consisting of: adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®), and at least a second additional therapeutic agent selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one, two, or three additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2; and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In a particular embodiment, a compound disclosed herein, or a pharmaceutically acceptable salt thereof, is combined with a first additional therapeutic agent selected from the group consisting of adefovir (HEPSERA®), tenofovir disoproxil fumarate (VIREAD®), tenofovir alafenamide, tenofovir, tenofovir disoproxil, tenofovir alafenamide fumarate, tenofovir alafenamide hemifumarate, entecavir (BARACLUDE®), telbivudine (TYZEKA®), or lamivudine (EPIVIR-HBV®); and one, two, three, or four additional therapeutic agents selected from the group consisting of immunomodulators, TLR7 modulators, TLR8 modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, stimulators of NOD2 HBV viral entry inhibitors, NTCP inhibitors, HBx inhibitors, cccDNA inhibitors, siRNA, miRNA gene therapy agents, sshRNAs, KDM5 inhibitors, and nucleoprotein modulators (HBV core or capsid protein modulators).

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula I (e.g., from 10 mg to 1000 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of Formula I) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., an inhibitor of NS5A or NS5B) may be combined with the agents provided herein in any dosage amount of the compound (e.g., from 50 mg to 500 mg of compound) the same as if each combination of dosages were specifically and individually listed.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

VII. EXAMPLES

Example 1: Antiviral Activity

Another aspect of the disclosure relates to methods of inhibiting viral infections, comprising the step of treating a sample or subject suspected of needing such inhibition with a composition of the disclosure.

Within the context of the disclosure samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and manmade materials such as cell cultures.

If desired, the anti-virus activity of a compound of the disclosure after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the disclosure can be measured using standard screening protocols that are known.

Example 2: Evaluation of Cell-Based Anti-HCV Activity

In order to evaluate a compound's ability to inhibit NS5A, NS5B or NS3, the following protocol may be employed.
Cell-Based NS5A Assay Antiviral potency ($EC_{50}$) is determined using a *Renilla* luciferase (RLuc)-based HCV replicon reporter assay. To perform the assay for genotype 1 and 2a JFH-1, stable HCV 1a RLuc replicon cells (harboring a dicistronic genotype 1a H77 replicon that encodes a RLuc reporter), stable HCV 1b RLuc replicon cells (harboring a dicistronic genotype 1b Con1 replicon that encodes a RLuc reporter), or stable HCV 2a JFH-1 Rluc replicon cells (harboring a dicistronic genotype 2a JFH-1 replicon that encodes a RLuc reporter; with L31 present in NS5A) are dispensed into 384-well plates for $EC_{50}$ assays. To perform the assay for genotype 2a (with M31 present in NS5A) or genotype 2b, NS5A chimeric genotype 2a JFH-1 replicons that encodes a RLuc-Neo reporter and either genotype 2a J6 strain NS5A gene or genotype 2b MD2b-1 strain NS5A gene (both with M31 present) respectively, are either transiently transfected (t) into Huh-Lunet cells or are established as stably replicating replicon cells(s). Either cells are dispensed into 384-well plates for $EC_{50}$ assays. To perform the assay for genotype 3 and genotype 4, NS5A chimeric genotype 1b Con1 replicons that encodes a Pi-RLuc reporter and either genotype 3a S52 strain NS5A gene or genotype 4a ED43 strain NS5A gene respectively, are transiently transfected (t) into Huh-Lunet cells, which are subsequently dispensed into 384-well plates. Compounds are dissolved in DMSO at a concentration of 10 mM and diluted in DMSO either manually or using an automated pipetting instrument. Serially 3-fold diluted compounds are either manually mixed with cell culture media and added to the seeded cells or directly added to the cells using an automated instrument. DMSO is used as a negative (solvent; no inhibition) control, and the protease inhibitor ITMN-191 is included at a concentration >100×$EC_{50}$ as a positive control. 72 hours later, cells are lysed and *Renilla* luciferase activity quantified as recommended by the manufacturer (Promega-Madison, Wis.). Non-linear regression was performed to calculate $EC_{50}$ values.

To determine the antiviral potency ($EC_{50}$) against resistance mutants, resistance mutations, including M28T, Q30R, Q30H, L31M, and Y93C in genotype 1a NS5A and Y93H in genotype 1b NS5A, are introduced individually into either 1a Pi-Rluc or 1b Pi-Rluc replicons by site directed mutagenesis. Replicon RNA of each resistant mutant was transiently transfected into Huh-7-derived cured-51 cells and antiviral potency is determined on these transfected cells as described above.

Cell-Based NS5B Assay

Each compound (serially diluted from 100 µM) is added to Huh7 ($2 \times 10^3$ cells/well), HepG2 ($2 \times 10^3$ cells/well), BxPC3 ($2 \times 10^3$ cells/well), or CEM ($5 \times 10^3$ cells/well) cells and allowed to incubate for 8 days at 37° C. A medium only control is used to determine the minimum absorbance value and an untreated cell. At the end of the growth period, MTS dye from the CellTiter 96 Aqueous One Solution Cell Proliferation Assay kit (Promega) is added to each well and the plate is incubated for an additional 2 hours. The absorbance at 490 nm is read with a Victor 3 plate reader (Perkin Elmer) using the medium only control wells as blanks. The 50% inhibition value ($CC_{50}$) is determined by comparing the absorbance in wells containing cells and test compound to untreated cell control wells.

The HCV NS5B reaction is performed in a 20 µL mixture containing varying concentrations of the test compound, 1 µM of all four natural ribonucleotides, [$\alpha$-$^{32}$P]UTP, 20 ng/µL of genotype 1b (−) IRES RNA template, 1 unit/µL of SUPERase•In (Ambion, Austin, Tex.), 40 ng/µL of wild type or S282T NS5B Genotype 1b, 1 mM $MgCl_2$, 0.75 mM $MnCl_2$, and 2 mM DTT in 50 mM Hepes buffer (pH 7.5). The reaction is quenched by adding 80 µL of stop solution (12.5 mM EDTA, 2.25 M NaCl, and 225 mM sodium citrate) after incubating at 27° C. for 30 minutes. The radioactive RNA products are separated from unreacted substrates by passing the quenched reaction mixture through a Hybond N+ membrane (GE Healthcare, Piscataway, N.J.) using a dot-blot apparatus. The RNA products are retained on the membrane and the free nucleotides are washed out. The membrane is washed 4 times with a solution containing 0.6 M NaCl and 60 mM sodium citrate. After rinsing the membrane with water followed by ethanol, the membrane is exposed to a phosphorscreen and the products are visualized and quantified using a phosphorimager. The $IC_{50}$ values are calculated using GraFit program version 5 (Erithacus Software, Horley, Surrey, UK). All the reactions are done in duplicate and the results are reported as $IC_{50}$±standard error.

Cell-Based NS3 Assay

Antiviral potency ($EC_{50}$) is determined in both stable subgenomic HCV replicon cell lines and transient-transfected HCV replicon cells. The term half maximal effective concentration ($EC_{50}$) refers to the concentration of a drug which induces a response halfway between the baseline and maximum after the exposure time specified.

Stable subgenomic HCV replicons for genotype 1a, 1b, 2a, 3a, and 4a are established in Huh-7-derived cells as described by Lohmann et al (Lohmann V, Korner F, Koch J, et al Replication of subgenomic hepatitis C virus RNAs in a hepatoma cell line, *Science* 1999; 285:119-3). Each stable cell line contains a bicistronic HCV replicon that encodes a humanized *Renilla* luciferase (hRLuc) reporter gene fused to a selectable neomycin-resistance gene, followed by an EMCV IRES and the NS3-NS5B coding region of HCV. Selection for cells constitutively expressing the HCV replicon is achieved in the presence of the selection antibiotic, neomycin (G418). Luciferase activity is measured as a marker for intracellular HCV replication levels.

The genotype 1a stable replicon is derived from the H77 HCV strain and contained adaptive mutations P1496L and S2204I. The genotype 1b stable replicon is derived from the Con1 HCV strain and contained adaptive mutations E1202G, T12801, and K1846T. The genotype 2a stable replicon is derived from the JFH-1 HCV strain and does not require adaptive mutations. The genotype 3a stable replicon is derived from the S52 HCV strain and contained adaptive mutations P1121L, A1198T and S2210I (equivalent to S2204I in genotype 1). The genotype 4a stable replicon is derived from the ED43 HCV strain and contained adaptive mutations Q1691R and S2204I. All replicon cell lines were propagated in Huh-7-derived cells and maintained in Dulbecco's modified Eagle's Medium (DMEM) supplemented with 10% fetal bovine serum (FBS) and 0.5 mg/ml G418.

Transient-transfected HCV replicons are established for genotype 1a, 1b, 3a and NS3/4a protease inhibitor resistant variants D168A in genotype 1b or R155K in genotype 1a. Transient-transfected replicons are also biscistronic subgenomic replicons but do not contain the neomycin selectable marker present in stable replicons. These replicons encode the poliovirus IRES followed by the hRLuc reporter gene, the EMCV IRES and finally the NS3-NS5B coding region of HCV. The genotype 1a (H77) and 1b (Con1) wild-type replicons are derived from the same strain and contain the same adaptive mutations as listed above. The genotype 3a transient replicon is derived from the S52 HCV strain as above, but contains slightly different adaptive mutations P1112L, K1615E and 52210I. Specifically, the secondary adaptive mutation A1198T (A166T) in the protease domain of the stable genotype 3a replicon is replaced with K1615E (K583E) in the NS3 helicase, with no effect on replication efficiency. Removal of A166T located in the protease domain minimizes the impact of this variant on inhibitors targeting the protease domain and represents a protease domain closer to wild type for genotype 3a. Resistant replicons encoding NS3/4 protease inhibitor mutations are introduced into the 1b or 1a wild-type NS3 gene by site directed mutagenesis. In vitro transcribed RNAs from all transient replicons are transfected into naive Huh-7-derived cell lines by electroporation. Luciferase activity is measured as a marker for intracellular HCV replication levels.

To perform $EC_{50}$ assays, cells from each HCV replicon are dispensed into 384-well plates. Compound(s) are dissolved in DMSO at a concentration of 10 mM and diluted in DMSO using an automated pipetting instrument. Three-fold serially diluted compounds are directly added to the cells using an automated instrument. DMSO is used as a negative (solvent; no inhibition) control, and a combination of three HCV inhibitors including a protease inhibitor; an NS5A inhibitor and a nucleoside inhibitor is used at concentrations >$100 \times EC_{50}$ as a positive control (100% inhibition). Seventy-two hours later, cells are lysed and *Renilla* luciferase activity are quantified as recommended by the manufacturer (Promega-Madison, Wis.). Non-linear regression is performed to calculate $EC_{50}$ values.

Example 3. Reduction of Hepatitis B Surface Antigen

Inhibitors described herein are tested for their ability to reduce hepatitis B surface antigen (HBsAg) based on the following protocol.

HBV Cell Line

HepG2.2.15 cells (Acs et al. Proc Natl Acad Sci USA, 84, (1987), 4641-4), a constitutively HBV-expressing cell line are cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells are seeded in duplicate into white, 96-well plates at 1.5×10 cells/well. The cells are treated with a three-fold serial dilution series of the compounds in DMSO. The final DMSO concentration in all wells is 1% and DMSO is used as no drug control.

The HBsAg chemiluminescence immunoassay (CLIA) kit (Autobio Diagnostics Co., Zhengzhou, China, Catalog number: CL0310-2) is used to measure the levels of secreted HBV antigens semi-quantitatively. For the detection 50 µL well culture supernatant is used and HBsAg is quantified using HBsAg chemiluminescence immunoassay (CLIA) kit (Autobio Diagnostics Co., Zhengzhou, China, Catalog number: C 1.0310-2), 50 µL of the supernatant is transferred to the CLIA assay plate and 50 µL of enzyme conjugate reagent is added into each well. The plates are sealed and gently agitated for 1 hour at room temperature. The supernatant-enzyme-mixture is discarded and wells are washed 6 times with 300 µL of PBS. The residual liquid is removed by plating the CLIA plate right side down on absorbent tissue paper. 25 µL of substrates A and B were added to each well. Luminance is measured using a luminometer (Mithras LB 940 Multimode Microplate Reader) after 10 minutes incubation. Dose response curves are generated and the $IC_{50}$ value is extrapolated by using the E-WorkBook Suite (ID Business Solutions Ltd., Guildford, UK). The $IC_{50}$ is defined as the compound concentration (or conditioned media log dilution) at which HBsAg secretion is reduced by 50% compared to the no drug control.

Example 4. HBV DNA Assay

A HBV DNA assay may also be employed to evaluate a test compound's activity in inhibiting HBV DNA replication. The assay employs real-time qPCR (Taq an) to directly measure extracellular HBV DNA copy number. HepG2.2.15 cells are plated in 96-well microtiter plates. On the following day, the HepG2.2. 1 5 cells are washed and the medium is replaced with complete medium containing various concentrations of a test compound in triplicate. 3TC is used as the positive control, while media alone is added to cells as a negative control (virus control, VC). Three days later, the culture medium is replaced with fresh medium containing the appropriately diluted drug. Six days following the initial administration of the test compound, the cell culture supernatant is collected, treated with pronase and then used in a real-time qPCR/TaqMan assay to determine HBV DNA copy numbers. Antiviral activity is calculated from the reduction in HBV DNA levels ($IC_{50}$).

Example 5. HBV Reduction in Patients

Efficacy may be tested in human patients according to a variety of protocols known in the art, such as Kim et al., "HBsAg level and clinical course in patients with chronic hepatitis B treated with nucleoside analogue: five years of follow-up data," Clin. Mol Hepatol., 2013, 19(4), 409-416 or Lee et al., "Quantitative hepatitis B surface antigen and hepatitis B e entigen titers in prediction of treatment response to entecavir, Hepatology, 2011, 53, 1486-1493.

Further, the Architect HBsAg quantitative kit is also available for purchase from Abbott Laboratories. The assay method is described below.

Methods

The ARCHITECT HBsAg assay is a two-step immunoassay, using chemiluminescent microparticle immunoassay (CMIA) technology, with flexible assay protocols, referred to as Chemiflex for the quantitative determination of HBsAg in human serum. In the first step, samples and anti-HBs coated paramagnetic microparticles are combined HBsAg present in the sample binds to the anti-HBs coated microparticles. After washing, acridinium-labeled anti-HBs conjugate is added in the second step. Following another wash cycle, Pre-trigger and Trigger Solutions are added to the reaction mixture. The resulting chemiluminescent reaction is measured as relative light units (RLUs). A direct relationship exists between the amount of HBsAg in the sample and the RLUs detected by the ARCHITECT i System optics.

The concentration of hepatitis B surface antigen in the specimen is determined using a previously generated ARCHITECT HBsAg calibration curve. If the concentration of the specimen is greater than or equal to 0.05 IU/mL, the specimen is considered reactive for HBsAg.

Specimen

Testing is performed on human serum. A minimum volume of 0.35 mL is requested. Specimens are shipped to Covance frozen on dry ice and are stable for 90 days at −70 C. The stability ambient is 3 days and the stability refrigerated is 7 days. Hepatitis B Surface Ag Quantitative testing has 5 days TAT and it is performed at the Geneva and Singapore CCLS facility.

Reagent

The ARCHITECT HBsAg Quantitative Reagent kit assay is manufactured by Abbott Ireland Diagnostic Division, Ireland.

Calibration

Abbott Laboratories provides the two HBsAg calibrators. A two-point calibration is performed once every six months, whenever a lot number change occurs or major system components are replaced.

Intra-Assay Precision

The manufacturer states expected intra-assay precision for HBsAg quantitative as 4.1-7.8% CV. The acceptable limit for CCLS is less than or equal to 6.9% CV. The following shows intra-assay precision determined by two quality controls tested in single run then evaluating the coefficient of variation (Statement of Claims Summary Report, May 2014):

|  | QC II | QC III |
|---|---|---|
| Mean (IU/mL) | 0.252 | 165.840 |
| SD | 0.011 | 6.336 |
| % CV | 4.2% | 3.8% |
| N | 20 | 20 |

Intra-Assay Precision

The manufacturer states expected inter-assay precision values for HBsAg quantitative as 6.2-9.2%. The acceptable limit CCLS is less than or equal to 9.1% CV. The following shows inter-assay precision determined by analysis of quality control material (May 2014):

|  | QC II | QC III |
|---|---|---|
| Mean (IU/mL) | 0.249 | 165.797 |
| SD | 0.007 | 10.429 |
| % CV | 3.0% | 6.3% |
| N | 10 | 10 |

Accuracy

Accuracy is an important parameter in the validation process. For certain assays, accuracy is assessed using standard validated reference materials (SVRM's) or primary reference materials that are available from the College of American Pathologists (CAP), and other sources such as National Institute of Standards and Technology (NIST) and other suppliers. In other cases, the results from proficiency testing (PT) that are obtained from agencies such as the CAP or other PT providers are used to establish accuracy. The example may also establish an accuracy statement using either assayed quality control samples provided from commercial sources or a split specimen study with a qualified reference laboratory or another laboratory.

Reportable Range

The reportable range for the HBsAg quantitative assay is 0.05-125000.00 IU/mL. The analytical measurement range is 0.05-250.00 IU/mL. Samples with HBsAg concentrations greater than 250.00 IU/mL are diluted up to a maximum dilution of 1:500, extending the upper reporting limit to 125000.00 IU/mL.

Specificity and Sensitivity

The assay is unaffected by icterus (bilirubin <342 μmol/L or <20 mg/dL), hemolysis (Hgb <0.311 mmol/L or <0.5 g/dL), lipemia (triglycerides <33.87 mmol/L or <3000 mg/dL), and protein <12 g/dL. In patients receiving therapy with biotin doses (i.e. >5 mg/day), no samples should be taken until at least 8 hours after the last biotin administration.

Results

Overall Specificity and Sensitivity

Overall specificity and sensitivity were estimated from the results of 6429 serum and plasma specimens, tested with ARCHITECT HBsAg at six clinical sites. HBV seroconversion panels results were excluded from this calculation because the panels contained multiple bleeds from the same individual. Only the plasma specimens from the matched serum/plasma pairs were used so that these specimens would be represented once.

The overall specificity was estimated to be 99.87% (6001/6009) with a 95% confidence interval of 99.74% to 99.94%. The overall sensitivity was estimated to be 99.52% (418/420) with a 95% confidence interval of 98.29% to 99.94%.

HBsAg Mutant Detection

HBsAg mutant susceptibility was evaluated with the ARCHITECT HBsAg assay.

The most prevalent HBsAg mutant, the Gly→Arg 145 mutant (Glycine [GLY] to Arginine [ARG] mutation at amino acid position 145 of HBsAg), was readily detected in the ARCHITECT HBsAg assay with a sensitivity equivalent to detection of wild type HBsAg30.

As can be seen in FIG. 1, after administration of a fixed dose combination of ledipasvir (90 mg) and sofosbuvir (400 mg) once daily, patients saw a reduction in HBsAg. This data was observed based on the clinical trial evaluating safety and efficacy of ledipasvir/sofosbuvir fixed dose combination in adults with chronic HCV and HBV co-infection. The patients were dosed for 12 weeks and suffered from chronic genotype 1 or 2 HCV and HBV.

Figure 2:
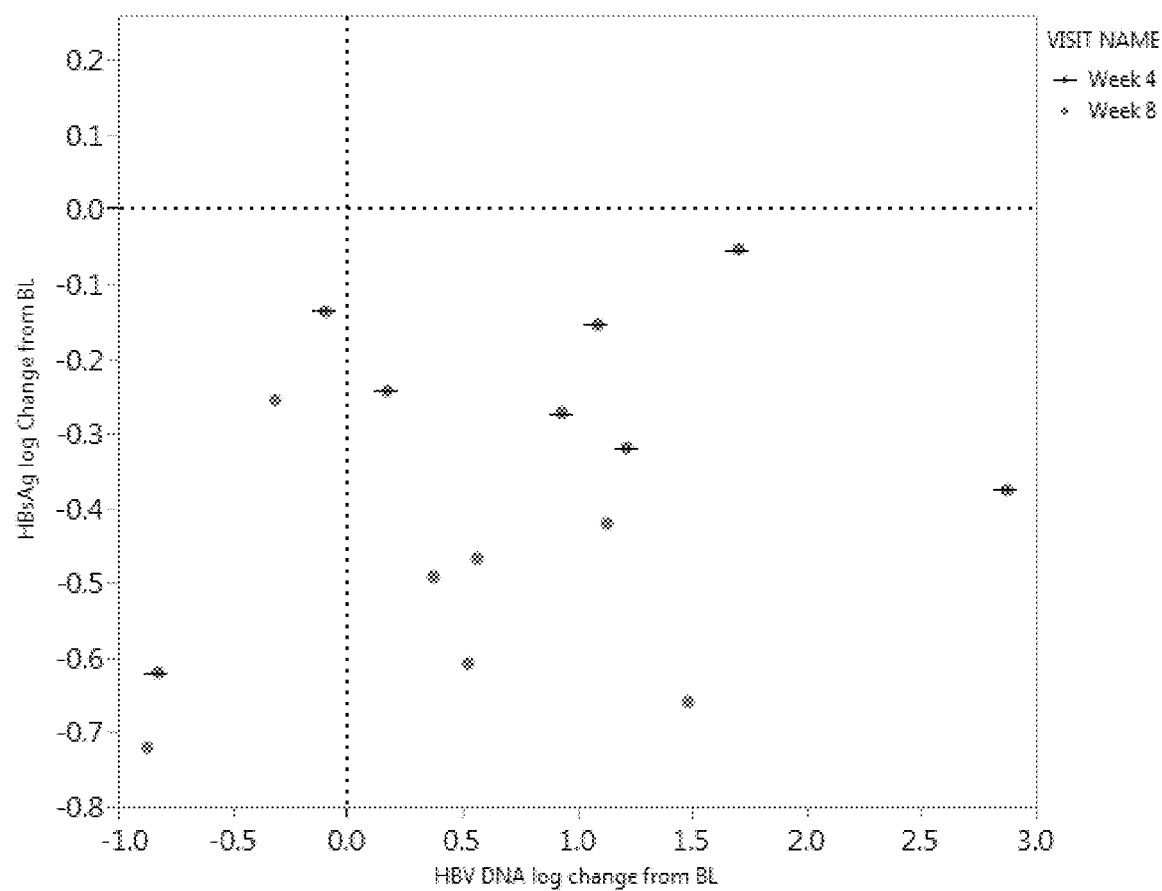
FIG. 2 shows the change in HBV DNA and HBsAG at week 4 and week 8 timepoints after administration of a fixed dose combination of ledipasvir and sofosbuvir.
Figure 3:
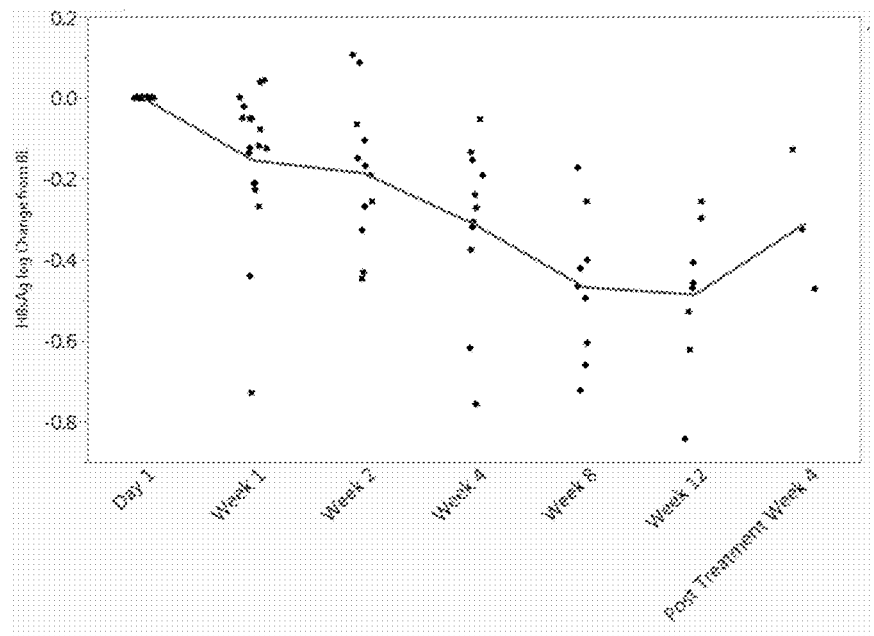
FIG. 3 shows the HBsAg and HBV DNA kinetics at various timepoints after administration of a fixed dose combination of ledipasvir and sofosbuvir.
Figure 3:
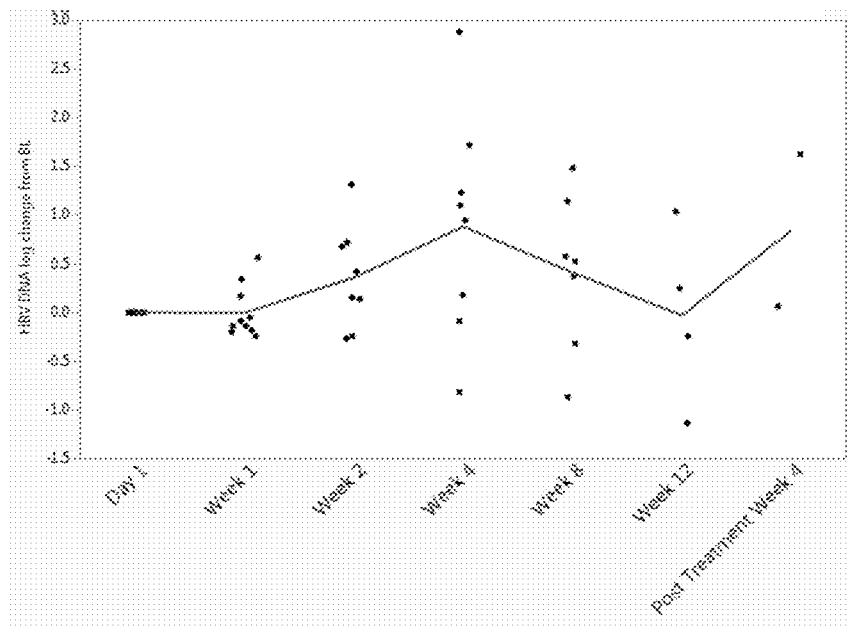
Figure 4:
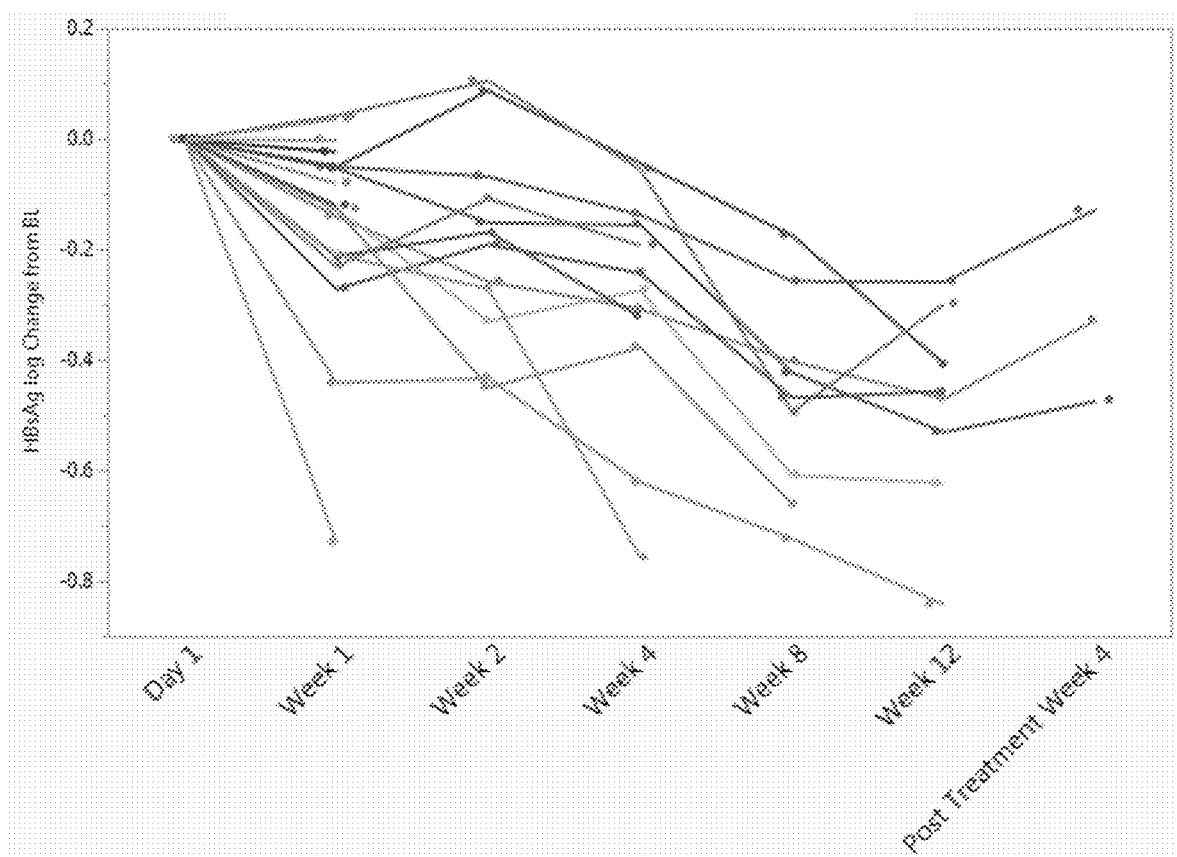
FIG. 4 shows the change from baseline in HBsAg after administration of a fixed dose combination of ledispavir and sofosbuvir.

Additional data acquired after administration of the combination are seen in FIGS. 2-4. As shown in FIG. 2, at week 8, the patients had more pronounced reduction of HBsAg than at week 4. The overall trend of the HBsAg reduction over the treatment period is apparent from FIG. 3, while there are more variabilities in the reduction of mean HBV DNA amounts. The changes of HBsAg in each individual patient are plotted in FIG. 4, and it can be seen that there is a universal reduction of HBsAg levels among all patients over time.

All publications, patents, and patent documents cited herein above are incorporated by reference herein, as though individually incorporated by reference.

The disclosure has been described with reference to various specific and preferred embodiments and techniques. However, one skilled in the art will understand that many variations and modifications may be made while remaining within the spirit and scope of the disclosure.

What is claimed is:

1. A method for treating a hepatitis B virus infection in a human in need thereof comprising administering an effective amount of ledipasvir and an effective amount of sofosbuvir and optionally a NS3 inhibitor, wherein the effective amount of ledipasvir and the effective amount of sofosbuvir is sufficient to lower the HBsAg level in the human.

2. The method of claim 1, wherein the human is administered about 90 milligrams of ledipasvir.

3. The method of claim 1, wherein the human is administered about 400 milligrams of sofosbuvir.

4. The method of claim 1, wherein the NS3 inhibitor is voxilaprevir.

5. The method of claim 1, wherein ledipasvir and sofosbuvir and optionally the NS3 inhibitor are administered together.

6. The method of claim 1, wherein ledipasvir and sofosbuvir and optionally the NS3 inhibitor are administered separately.

7. The method of claim 1, further comprising administering to the human an effective amount of a reverse transcriptase inhibitor.

8. The method of claim 7, wherein the reverse transcriptase inhibitor is tenofovir alafenamide.

9. The method of claim 8, wherein the human is administered about 25 mg tenofovir alafenamide.

10. The method of claim 1, wherein the human is co-infected with human immunodeficiency virus (HIV).

11. The method of claim 1, wherein the human is not co-infected with hepatitis C virus (HCV).

12. A method for treating a hepatitis B virus infection in a human in need thereof comprising administering an effective amount of ledipasvir and an effective amount of sofosbuvir and optionally a NS3 inhibitor, wherein the human is not co-infected with hepatitis C virus (HCV).

13. The method of claim 12, wherein the human is administered about 90 milligrams of ledipasvir.

14. The method of claim 12, wherein the human is administered about 400 milligrams of sofosbuvir.

15. The method of claim 12, wherein the NS3 inhibitor is voxilaprevir.

16. The method of claim 12, wherein ledipasvir and sofosbuvir and optionally the NS3 inhibitor are administered together.

17. The method of claim 12, wherein ledipasvir and sofosbuvir and optionally the NS3 inhibitor are administered separately.

18. The method of claim 12, further comprising administering to the human an effective amount of a reverse transcriptase inhibitor.

19. The method of claim 18, wherein the reverse transcriptase inhibitor is tenofovir alafenamide.

20. The method of claim 19, wherein the human is administered about 25 mg tenofovir alafenamide.

21. The method of claim 12, wherein the human is co-infected with human immunodeficiency virus (HIV).

* * * * *